United States Patent [19]

Betz et al.

[11] Patent Number: 5,607,580
[45] Date of Patent: Mar. 4, 1997

[54] NUCLEOPHILIC BODIES BONDED TO SILOXANE AND USE THEREOF FOR SEPARATIONS FROM SAMPLE MATRICES

[75] Inventors: William R. Betz, Bellefonte; James L. Desorcie, State College, both of Pa.

[73] Assignee: Supelco, Inc., Bellefonte, Pa.

[21] Appl. No.: 473,239

[22] Filed: Jun. 7, 1995

Related U.S. Application Data

[60] Division of Ser. No. 283,210, Jul. 29, 1994, which is a continuation-in-part of Ser. No. 276,048, Jul. 15, 1994, abandoned, which is a continuation-in-part of Ser. No. 201,752, Feb. 25, 1994, abandoned, which is a continuation-in-part of Ser. No. 191,644, Feb. 4, 1994, abandoned.

[51] Int. Cl.$^6$ .................................................. B01D 15/08
[52] U.S. Cl. ........................... 210/198.2; 210/502.1; 210/635; 210/656; 95/88; 96/101
[58] Field of Search .................... 95/88; 96/101; 210/635, 656, 658, 198.2, 198.3, 502.1

[56] References Cited

U.S. PATENT DOCUMENTS

| | | | |
|---|---|---|---|
| H896 | 3/1991 | Szakasits et al. | 210/198.2 |
| 3,182,394 | 10/1962 | Jentzsch | 29/460 |
| 3,295,296 | 10/1963 | Halasz et al. | 55/67 |
| 3,418,152 | 12/1968 | Staudenmayer | 117/63 |
| 3,514,925 | 6/1970 | Bossart | 55/386 |
| 3,647,684 | 3/1972 | Malcolm et al. | 210/31 |
| 3,772,909 | 11/1973 | Anderson | 73/23.1 |
| 3,808,125 | 4/1974 | Good | 210/31 C |
| 3,822,530 | 7/1974 | Fuller et al. | 55/67 |
| 3,866,308 | 2/1975 | Halasz et al. | 29/527.4 |
| 3,922,392 | 11/1975 | Kohlschutter | 427/215 |
| 3,988,919 | 11/1976 | Talmi et al. | 73/23.1 |
| 4,043,905 | 8/1977 | Novotny et al. | 210/31 C |
| 4,063,911 | 12/1977 | Kruppa et al. | 55/67 |
| 4,128,438 | 12/1978 | Wolff et al. | 106/307 |
| 4,169,790 | 10/1979 | Pretorius et al. | 210/31 C |
| 4,207,188 | 6/1980 | Tsuda et al. | 210/198 C |
| 4,218,359 | 8/1980 | Marwitz et al. | 260/33.8 SB |
| 4,276,061 | 6/1981 | Nestrick et al. | 55/67 |
| 4,292,362 | 9/1981 | Marwitz et al. | 428/254 |
| 4,293,415 | 10/1981 | Bente, III et al. | 210/198.2 |
| 4,376,641 | 3/1983 | Nestrick et al. | 55/67 |
| 4,509,964 | 4/1985 | Hubball et al. | 55/386 |
| 4,578,084 | 3/1986 | Kakinoki et al. | 8/115.61 |
| 4,692,474 | 9/1987 | Mayer et al. | 521/88 |

(List continued on next page.)

FOREIGN PATENT DOCUMENTS

| | | | |
|---|---|---|---|
| 0425104A1 | 5/1991 | European Pat. Off. | 210/198.2 |
| 0544450A1 | 6/1993 | European Pat. Off. | 210/198.2 |

OTHER PUBLICATIONS

Mikes Laboratory Handbook of Chromatographic and Allied Methods, John Wiley & Sons, 1979, New York, pp. 525–527.

(List continued on next page.)

*Primary Examiner*—Ernest G. Therkorn
*Attorney, Agent, or Firm*—Senniger, Powers, Leavitt & Roedel

[57] ABSTRACT

A structure comprising bodies having a functional surface property bonded to a substrate via a siloxane polymer adhesive. The structure may comprise a novel composition comprising a siloxane polymer having carbon bodies bonded thereto by direct carbon to silicon bonds. This composition may be used to bond carbon particles through a medium comprising the siloxane polymer to a vitreous, metal, plastic or other nucleophilic substrate. Alternatively, the bodies may comprise alumina, silicon, zeolite, organic polymers or other nucleophilic compositions, which are bonded directly to silicon atoms of the siloxane polymer. To bond carbon or other nucleophilic bodies to the substrate, the substrate is contacted with a mixture of the bodies and a hydrosiloxane polymer. The mixture is heated to cause the polymer to be bonded to the nucleophilic bodies, typically by C—Si, C—O—Si, Si—O—Si or Si—O—Al bonds, and to the substrate by reaction with the surface silanol or other nucleophilic groups. Chromatographic methods using a column comprising the novel composition are also disclosed.

20 Claims, 15 Drawing Sheets

U.S. PATENT DOCUMENTS

| | | | |
|---|---|---|---|
| 4,741,830 | 5/1988 | Hauck et al. | 210/635 |
| 4,743,377 | 5/1988 | Ohtsu et al. | 210/635 |
| 4,746,572 | 5/1988 | Glajch et al. | 428/403 |
| 4,756,971 | 7/1988 | Virtanen et al. | 428/405 |
| 4,789,479 | 12/1988 | Onitsuka et al. | 210/635 |
| 4,793,920 | 12/1988 | Cortes et al. | 210/198.2 |
| 4,835,058 | 5/1989 | Komiya et al. | 428/405 |
| 4,839,331 | 6/1989 | Maroldo et al. | 502/416 |
| 4,895,968 | 1/1990 | Buese et al. | 556/462 |
| 4,900,779 | 2/1990 | Leibfried | 524/862 |
| 4,909,935 | 3/1990 | Bradshaw et al. | 210/198.2 |
| 4,966,785 | 10/1990 | Springston | 427/39 |
| 4,967,897 | 11/1990 | Lachonius et al. | 198/841 |
| 4,968,760 | 11/1990 | Schiller et al. | 525/477 |
| 5,015,715 | 5/1991 | Divers et al. | 528/15 |
| 5,071,565 | 12/1991 | Fritz et al. | 210/692 |
| 5,082,559 | 1/1992 | Eguchi et al. | 210/198.2 |
| 5,094,754 | 3/1992 | Maroldo et al. | 210/635 |
| 5,098,784 | 3/1992 | Ichikawa et al. | 428/332 |
| 5,104,530 | 4/1992 | Maroldo et al. | 210/198.2 |
| 5,128,494 | 7/1992 | Blum | 556/457 |
| 5,135,649 | 8/1992 | Kanda et al. | 210/198.2 |
| 5,159,009 | 10/1992 | Wolff et al. | 524/495 |
| 5,194,333 | 3/1993 | Ohnaka et al. | 428/405 |
| 5,268,442 | 12/1993 | Bradshaw et al. | 528/25 |
| 5,271,833 | 12/1993 | Funkenbusch et al. | 210/198.2 |
| 5,279,742 | 1/1994 | Markell et al. | 210/638 |
| 5,308,481 | 5/1994 | Stalling et al. | 210/198.2 |
| 5,314,533 | 5/1994 | Goebel et al. | 106/287.13 |

OTHER PUBLICATIONS

Vidal–Madjar et al., "Fast Analysis of Geometrical Isomers of Complex Compounds by Gas–Solid Chromatography", Gas Chromatography Elsevier, Amsterdam 1970, pp. 20–23.

Petrarch Systems, "T–Structure Polydimethylsiloxanes with Functionality at Branch Terminus", undated pp. 175–177.

Novotny, et al., "Selective Monomolecular Layers for Improved Wettability of Glass Capillary Columns for Gas–Liquid Chromatography", Journal of Chromatography, vol. 84, 1973, pp. 167–170.

Novotny et al., "Some Factors Affecting the Coating of Open Tubular Columns for Gas Chromatography", Journal of Chromatographic Science, vol. 8, Jul. 1970, pp. 390–393.

Nikelly, J. G., "Preparation of Porous Layer Open Tubular Columns by the Dynamic Method", Analytical Chemistry, vol. 44, No. 3, Mar. 1972, pp. 623–625.

Hollis, O. L., "Porous Polymers Used in GC and LC", Journal of Chromatographic Science, vol. 11, Jul. 1973, pp. 335–342.

Bartle, et al., "Correlations of Surface Measurements with the Chromatographic Performance of Chemically Modified Glass Capillary Columns", Journal of Chromatography, vol. 94, 1974, pp. 35–51.

P. Arpino et al., "Production of Citral From Geraniol", Journal of Chromatography, vol. 138, 1977, pp. 173–182.

Vidal–Madjar, et al., "Gas–Solid and Gas–Liquid Chromatography Using Porous Layer Open Tube Columns Made With Graphitized Thermal Carbon Black", Analytical Chemistry, vol. 49, No. 6, May 1977, pp. 768–772.

Welsch, et al., "Properties of Micro–Packed Columns and of Porous–Layer Open–Tubular Columns with Graphitized Thermal Carbon Black", Journal of Chromatography, vol. 148 (1978) pp. 143–149.

Liberti et al., "Development of Porous–Layer Capillary Columns", Journal of Chromatography, vol. 279, 1983, pp. 1–8.

Zeeuw et al., "PoraPLOT Q: A Porous Layer Open Tubular Column with Styrene–Divinylbenzene Copolymer", Journal of High Resolution Chromatography & Chromatography Communications, vol. 11, Feb. 1988, pp. 162–167.

W. Betz, "Analysis of Permanent Gases, C2 and C3 Hydrocarbons Using Carboxen™ Micropaked and Porous Layer Open Tubular (PLOT) Capillary Columns", vol. 13, No. 4, pp. 2–4 Undated.

WO 9,301,494, (Abstract Only), Jan. 1, 1993 (PCT Application).

Stevens, et al., "Sampling and Analysis of Atmospheric Sulfates and Related Species", pp. 55–58 Undated.

Novotny, et al., "Surface Chemistry of Glass Open Tubular (Capillary) Columns Used in Gas–Liquid Chromatography", Chromatographia, vol. 7, No. 3, Mar. 1974, pp. 122–127.

Shaw, et al. "Measurement of Atmospheric Nitrate and Nitric Acid: The Denuder Difference Experiment", Atmospheric Environment, vol. 16, No. 4, 1982, pp. 845–853.

"New GC Columns For Faster, Better Separations", Supelco, vol. 13, No. 3, p. 15 Undated.

Betz, et al., "Gas Chromatographic Performance Characteristics of Micropacked Caillary Columns Containing Various Carbon Molecular Sieves and Graphitized Carbon Blacks", Supelco, five pages Undated.

West, et al., "C60 Siloxane Polymers From Hydrosilylation Reactions", Polymer Preprints, vol. 34, No. 1, 1993, p. 227.

J. G. Nikelly, "Dynamically Coated PLOT Columns", Analytical Chemistry, vol. 45, No. 13, Nov. 1973, pp. 2279–2281.

J. G. Nikelly, "Evaluation and Applications of Porous Layer Open Tubular Columns Made by the Dynamic Method", Analytical Chemistry, vol. 44, No. 3, Mar. 1972, pp. 625–627.

Stalling et al. "Fullerene–Linked Particles as LC Chromatographic Media and Modification of their Electron Donor/Acceptor Properties by Secondary Chemical Reactions", J. Microcolumn Separations, vol. 5, No. 3, 1993, pp. 223–235.

"The potential uses of bonded liquid crystal materials in high–performance liquid chromatography and surpercritical–fluid chromatography" Trends in Analytical Chemistry 11 (1992) Aug., No. 7, Amsterdam, NL pp. 259–266.

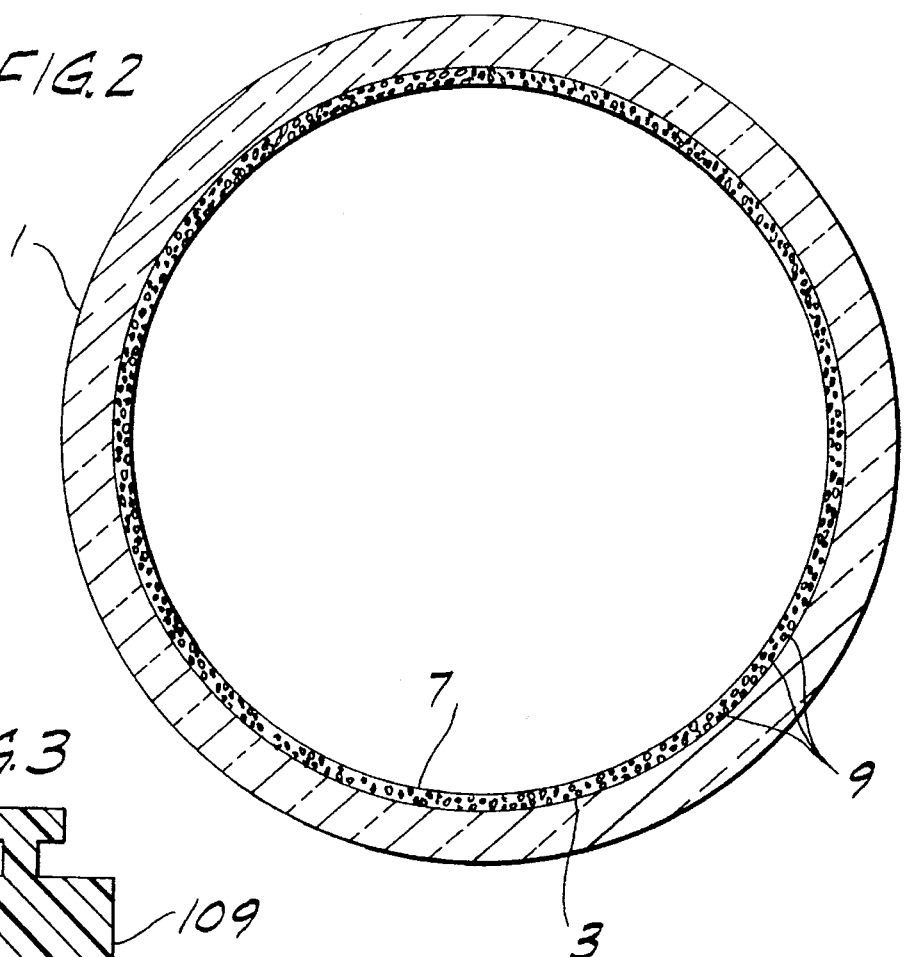
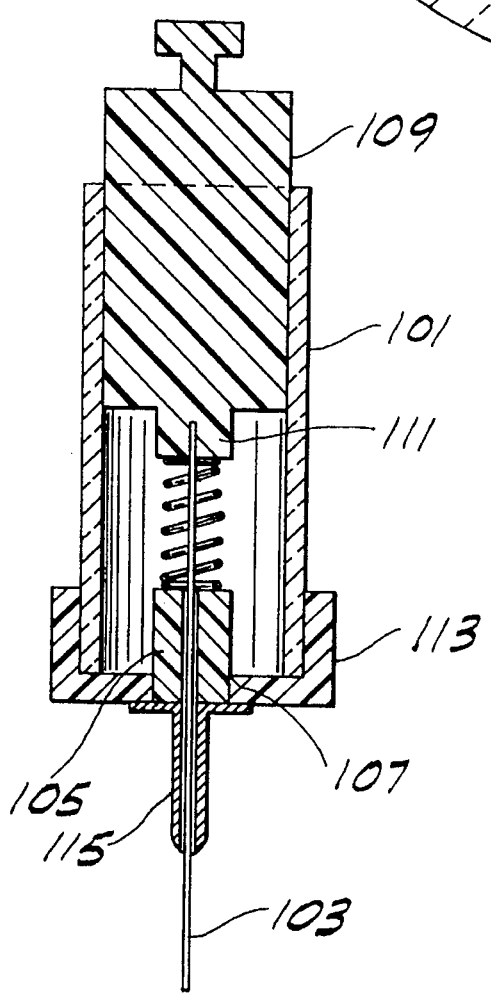
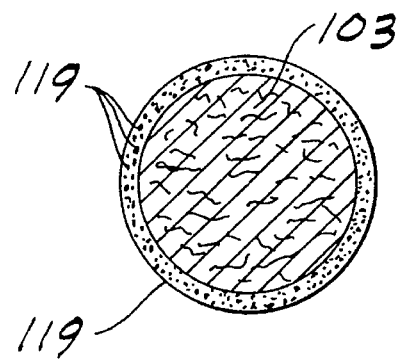

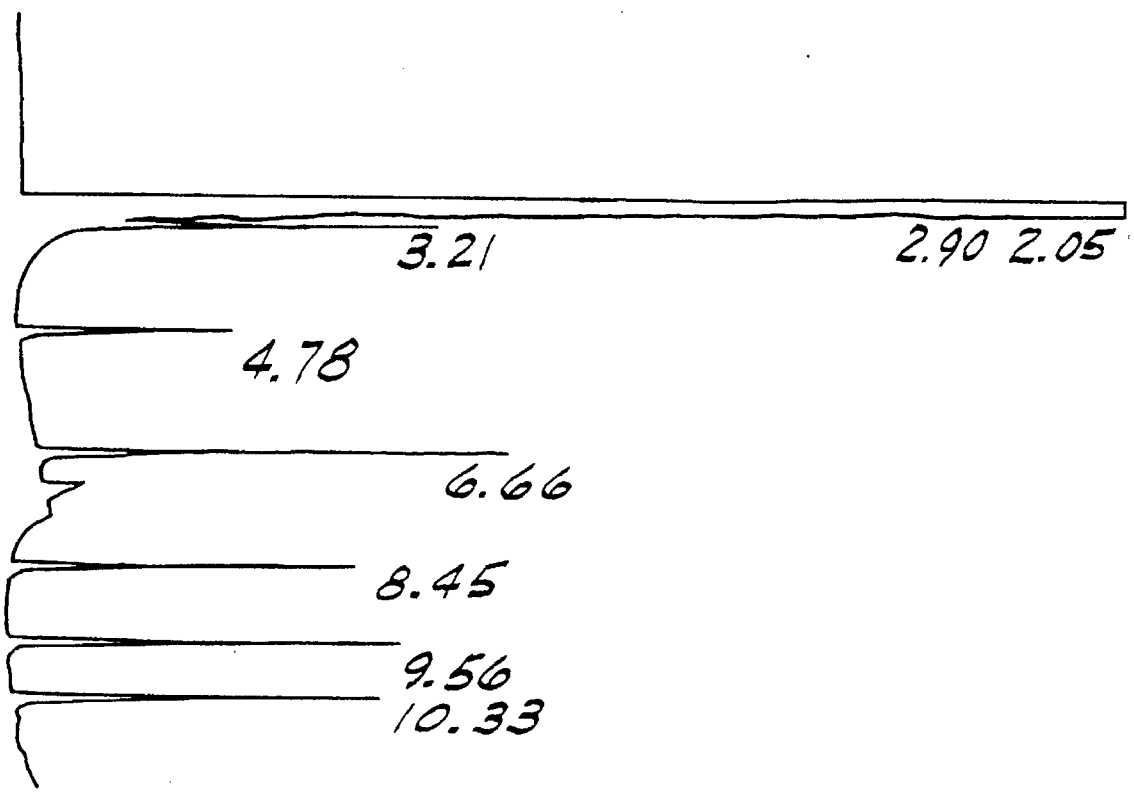

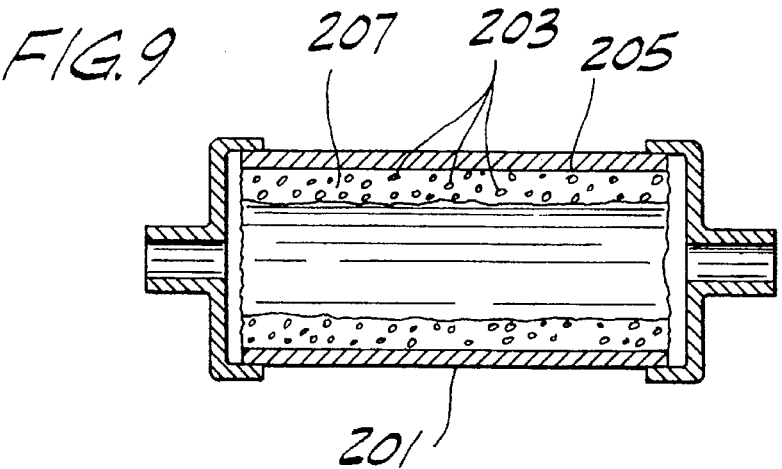
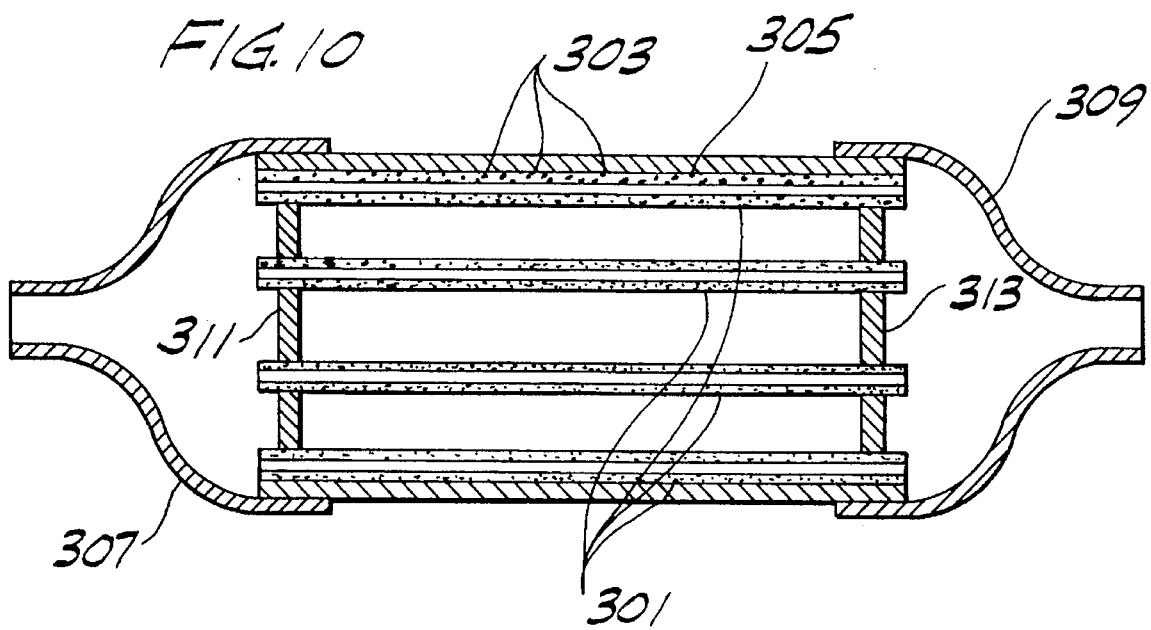

NUCLEOPHILIC BODIES BONDED TO SILOXANE AND USE THEREOF FOR SEPARATIONS FROM SAMPLE MATRICES

This is a division of application Ser. No. 08/283,210, filed Jul. 29, 1994, which is a continuation-in-part of Ser. No. 08/276,048, filed Jul. 15, 1994, now abandoned which is a continuation-in-part of Ser. No. 08/201,752, filed Feb. 25, 1994, now abandoned which is a continuation-in-part of Ser. No. 08/191,644, filed Feb. 4, 1994.

BACKGROUND OF THE INVENTION

This invention relates to separation of mixtures by differential adsorption, and more particularly to improved adsorption systems in which adsorbent bodies comprising a nucleophilic material, such as carbon, silica, alumina or a polymer having a hydrocarbon moiety, are bonded to a substrate via a siloxane polymer. Adsorbent bodies comprising carbon are preferably bonded to the siloxane polymer via a direct C—Si bond.

Various forms of carbon sere as effective media for chromatographic columns and solid phase extraction devices. Conventionally, where carbon has served as the stationary phase of a chromatographic column, the carbon is present in the column in the form of packing. However, when a sample matrix fluid is passed as the mobile phase through a column containing a fine carbon packing, the pressure drop through the column is generally high. Moreover, there is a tendency for the carbon to become entrained in the matrix fluid. Both entrainment and pressure drop can be minimized by using a granular carbon of relatively large particle size, but such coarse packing has a low adsorptive surface area per unit of column length and/or low resolution of the introduced analytes.

Adsorbent bodies of other nucleophilic materials, such as alumina, silica, zeolite and porous polymers are preferably also of small particle size; and packed columns containing such adsorbent materials typically present the same pressure drop and entrainment problems as packed carbon columns.

By binding a relatively fine carbon or other adsorbent material to the internal wall of a tube, a chromatographic apparatus may be provided which presents a substantial adsorptive surface area, yet may be operated at low pressure drop. By binding a high surface area adsorbent to the interior wall of a column, a column of a given diameter can accommodate a given flow of sample matrix at a much lower pressure drop than a column that is packed with an adsorbent of comparable particle size, and comparable adsorptive surface area per unit of column length. Consequently, at comparable pressure drop, the coated wall column can be of much smaller diameter than the packed column.

It has been found that much enhanced separation is achieved in columns of very small diameter, especially those in the capillary range, since axial backmixing is greatly minimized. Various adsorbent materials are used in such columns, including porous silica, zeolite molecular sieves and various forms of carbon. Such columns are generally referred to as "porous layer open tubular" (or PLOT) columns. Where a liquid stationary phase is coated over a porous support, the column may be referred to as "support coated open tubular (or SCOT). If the adsorbent material is carbon or graphite, capillary columns of this type are conventionally referred to "carbon layer open tubular" (CLOT) or "graphite layer open tubular" (GLOT). All operate at low pressure drop by providing an essentially unobstructed path for the mobile phase to flow over the porous adsorbent or support.

Activated charcoal particles have been coated onto the interior wall of a glass column by using high molecular weight waxes or organic liquids as binding agents. For example, Vidal-Madjar et al., "Fast Analysis of Geometrical Isomers of Complex Compounds by Gas-Solid Chromatography," *Gas Chromatograph*, Elsevier (Amsterdam 1970), pp. 20–23, describe the preparation of a capillary column containing graphitized carbon adhered to the interior column wall using a styrene polymer as a form of adhesive. Another common coating material used for this purpose is polyethylene glycol, typically modified to contain a carboxyl functionality for greater polarity. Carbon, zeolite, alumina and silica adsorbent particles have been adhered to the interior wall of a PLOT column using such coatings. However, the coating materials of the above described type bind to adsorbent bodies via Van der Waals forces only. Consequently, the column must be operated below the temperature at which the wax, polystyrene, polyethylene glycol or other bonding agent softens, or else the bond between carbon and the glass loses strength sufficient to resist entrainment. Typically, this means that the column cannot be operated above a limit of about 115° C. Even at temperatures below such limit, the carbon or other adsorbent particles have a tendency to break free into the matrix phase as it moves through the column. Moreover, the adsorbent particles are especially prone to entrainment in rinsing liquids or purging gases, which typically move at higher velocities than the sample matrix.

Solid phase extraction devices are advantageously constructed of a single fiber that may be injected into a sample via the cannula of a syringe; or bundle or cluster of fibers, for example, fibers arrayed in parallel in a manner similar to the bristles of a brush. Particles of adsorptive material are coated onto the fiber. In other devices known to the art, the adsorbent particles are enmeshed or otherwise mechanically trapped in a woven or blown fiber fabric, typically formed as or cut into a disk. Immersion of the device in a liquid sample matrix presents a large area of adsorptive surface on which a solute may be extracted from the matrix. A type of solid phase extraction device, commonly referred to as a "denuder," is used for selective removal of a component of a gas sample, such as an air sample. The adsorptive agent of a said phase extraction device is typically coated onto the surface of glass fibers in a manner comparable to the attachment of adsorptive particles to the inside wall of a chromatographic column as described above. Thus, activated carbon and other solid phase extraction devices known to the art have suffered from the same disadvantages as their chromatographic counterparts. Operating temperatures are limited; and the adsorptive particles are rather readily wiped off the fiber surfaces by contact with a sample matrix or rinsing liquid.

The tubular walls of chromatographic columns and the fibers of solid phase extraction devices are both preferably constituted of glass. However, a variety of metals and plastic materials may also be suitable, especially as materials for the walls of a chromatographic column.

A need has existed for an improved means of adhering carbon zeolite, alumina, silica and adsorptive organic polymer particles to the tubular walls of chromatographic columns and the exterior surfaces of the fibers of solid phase extraction devices. A particular need has existed for adhesives which bond effectively both the materials of an adsorbent body, such as carbon, zeolite, alumina, silica, and porous organic polymers, and to the materials of the column wall or fiber surface, such as glass, metal or plastic. Since glass is ordinarily the preferred material of construction for both column tubes and the fibers of extraction devices, there has been a particular need for a better form of adhesion of carbon to glass. It has been known that C—OH groups at the surfaces of carbon particles react with silanizing agents, such as dimethyldichlorosilane, to produce an Si—O—C bond. However, this form of bonding has not heretofore been recognized as effective for attaching adsorbent carbon or adsorptive polymer particles to either the internal wall of a glass chromatographic column or the exterior surface of the glass fibers of a solid phase extraction device. It has also been known in the art that direct C—Si bonds can be formed at high temperature by solid phase reaction between carbon and silicon, resulting in the formation of silicon carbide, which is well known for use as an abrasive but has not had application to the field of chemical separations.

Recently, the literature has reported hydrosilylation reactions of buckminsterfullerene, $C_{60}$, with various silanes West et al "$C_{60}$-Siloxane Polymers from Hydrosilylation Reactions," *Polymer Preprints*, Vol. 34, No. 1 (1993) describes the reaction of $C_{60}$ with methyldimethoxysilane, $H(Me_2SiO)_3SiMe_2H$, and $Me_3SiO$- (—$HSiMeO)_n$-(n-$OctSiMeO)_{3n}$-$SiMe_3$ (DP=30), respectively. The authors describe the resulting products as $C_{60}$ molecules surrounded and encapsulated by the bound polysiloxane. However, no utility is suggested for these compositions.

U.S. Pat. No. 5,308,481 describes a polymeric or siliceous support particle suitable for use in chromatographic separations having a buckminsterfullerene covalently bonded thereto. In bonding the buckminsterfullerene to a siliceous particle, the surface of the silica may be modified by bonding a silane thereto, heating to polymerize the resulting silicon layer and attaching the buckminsterfullerene to the resultant silicone polymer via a functionality on the fullerene. For example, the '481 patent describes reacting a fullerene with a diphenylmethyl silane functionalized silica gel in the presence of aluminum chloride to produce a structure in which the fullerene is bound to the silica through an O—SiR—$C_6H_4$ linkage.

A general need has existed in the art for securely adhering carbon or other granular or particulate bodies to the surface of a substrate. By way of particular example, it may be desirable to adhere catalyst bodies to the wall of reactor vessel, exhaust converter or other tubular fluid flow conduit. Further applications exist in which it may be desirable to adhere fibrous bodies to a substrate surface.

SUMMARY OF THE INVENTION

Among the several objects of the present invention, may be noted the provision of an improved means of bonding between bodies of granular, particulate or fibrous material and a substrate; the provision of such means for bonding the substrate material of a chromatographic column or solid phase extraction device and the material of an adsorbent particle such as carbon, zeolite, alumina, silica and organic polymers, and in particular for the bonding of elemental carbon and vitreous substrates such as silica glasses; the provision of such a bonding means which is stable at temperatures well in excess of 115° C., and preferably in excess of 300° C.; the provision of such bonding means by which carbon or other adsorbent material may be adhered to a glass, metal, or plastic substrate; and the provision of such bonding means by which adsorbent material can be bonded to the internal wall of a chromatographic column or the fibers of a solid phase extractive device.

Further objects of the invention include the provision of an improved chromatographic column containing a carbon, zeolite, alumina, silica or polymeric adsorbent; the provision of such a column which has a large carbon B.E.T. surface area per unit length of column or which contains graphite with effective adsorptive properties; the provision of such a column which can be of very small diameter yet be operated at low pressure drop; the provision of such a column which can be operated under varying conditions, including high temperature, without entrainment of adsorbent particles in a sample matrix phase; and the provision of such a column which can be vigorously rinsed without loss of adsorbent particles. Objects of the invention further include the provision of a solid phase extraction device in which adsorbent particles are adhered to glass fibers; the provision of such a device which can be used at high temperature without detachment of adsorbent particles; the provision of such a device which can be vigorously rinsed without loss of adsorbent particles; and the provision of means for bonding bodies of a catalytic material to a substrate.

It is a further object of the invention to provide methods for producing the bonding means, chromatographic columns, solid phase extraction devices and catalytic systems having the characteristics outlined above.

Briefly, therefore, the present invention is directed to a composition comprising a siloxane polymer having bodies of a carbonaceous material bonded thereto. The carbonaceous bodies comprise elemental carbon or a polymer comprising a hydrocarbon moiety. The bodies are bonded to the siloxane polymer by direct carbon to silicon bonds between carbon atoms of the bodies and silicon atoms of the siloxane polymer.

The invention is further directed to a structure comprising bodies having a functional surface property bonded to a substrate via a siloxane polymer adhesive. The bodies comprise a nucleophilic composition bonded directly to silicon atoms of the siloxane polymer.

The invention is further directed to a chromatographic apparatus comprising a column containing a substrate having adsorbent bodies bonded thereto through a medium comprising a siloxane polymer. The bodies comprise a nucleophilic composition bonded directly to silicon atoms of the siloxane polymer.

The invention further contemplates a structure comprising discrete adsorbent bodies bonded to a monolithic substrate through a medium comprising a siloxane polymer.

The invention further comprises a chromatographic apparatus comprising a column containing a substrate having adsorbent bodies bonded thereto through a medium comprising a siloxane polymer. The bodies comprise nucleophilic composition selected from among amorphous carbon, graphite, turbostatic carbon, zeolite, alumina, silica, and an organic polymer.

The invention is further directed to a chromatographic apparatus comprising a column containing a substrate having adsorbent particles bonded thereto through a medium comprising a siloxane polymer. The particles comprise a nucleophilic composition and have an average particle size of between about 0.1 and about 10 microns.

The invention is still further directed to a solid phase adsorption device comprising a fiber having adsorbent bodies adhered to a surface thereof through a medium comprising a siloxane polymer. The bodies comprise the nucleophilic composition bonded directly to silicon atoms of the siloxane polymer.

The invention is further directed to a chromatographic apparatus comprising a column containing a substrate having adsorbent bodies of a carbonaceous material bonded thereto through a medium comprising a siloxane polymer. The carbonaceous material is selected from among carbon and a polymer comprising a hydrocarbon moiety. The adsorbent bodies are bonded to the siloxane polymer via a C—O—Si linkage.

The invention is also directed to a solid phase adsorption device comprising fibers having adsorbent bodies of a carbonaceous material bonded thereto through a medium comprising a siloxane polymer. The carbonaceous material is selected from the group consisting of carbon and a polymer comprising a hydrocarbon moiety. The adsorbent bodies are bonded to the siloxane polymer via a C—O—Si linkage.

Further contemplated by the invention is a method for bonding bodies having a functional surface property to a substrate through a medium comprising a siloxane polymer. The bodies comprise a nucleophilic composition. In the method, the substrate is contacted with a mixture of the bodies and a hydrosiloxane or halosiloxane polymer. The mixture is heated to cause the polymer to be bonded to the bodies and to the substrate.

The invention is further directed to a solid phase adsorption device comprising a substrate having adsorbent bodies bonded thereto through a medium comprising a siloxane polymer. The bodies comprise a nucleophilic composition selected from among amorphous carbon, graphite, turbostatic carbon, zeolite, alumina, silica, and an organic polymer.

The invention is further directed to a solid phase adsorption device comprising a substrate having adsorbent particles bonded thereto through a medium comprising a siloxane polymer. The particles comprise a nucleophilic composition and have an average particle size of between about 0.1 and about 10 microns.

The invention is further directed to a chromatographic method for separation of a mixture of compounds. The mixture is introduced into a chromatographic column containing a substrate having adsorbent bodies bonded thereto through a medium comprising a siloxane polymer. The adsorbent bodies comprise a nucleophilic composition bonded directly to silicon atoms of the siloxane polymer. Components of the mixture are eluted from the column.

Other objects and features will be in part apparent and in part pointed out hereinafter.

BRIEF DESCRIPTION OF THE DRAWINGS

FIG. 2 is a schematic drawing corresponding to the photomicrograph of FIG. 1;

FIG. 3 illustrates a solid phase extraction device comprising a syringe containing a fiber having a coating of adsorbent particles embedded in a siloxane polymer webbing;

FIG. 4 is a transverse cross section of one of the fibers of FIG. 3 illustrating multiple layers of adsorbent particles embedded in a siloxane polymer webbing attached to the exterior surface of the fiber;

FIGS. 5 to 8 are chromatograms obtained by gas chromatography of various mixtures using a PLOT column of the type illustrated in FIGS. 1 and 2;

FIGS. 9 and 10 are schematic illustrations of "denuder" type solid phase adsorption devices utilized for removing select components of an air stream or other gas sample.

Corresponding reference characters indicate corresponding parts in the several views of the drawings.

DESCRIPTION OF THE PREFERRED EMBODIMENTS

Figure 1:
FIG. 1 is a photomicrograph of a transverse cross section of a tubular glass column wall having multiple layers of carbon particles embedded in a siloxane polymer webbing attached to the interior surface of the wall.

In accordance with the invention, bodies of granular particulate or fibrous material are bonded to a substrate via a medium comprising a siloxane polymer adhesive. As used herein, the term "functional surface property" means that the surface is capable of some physical or chemical function such as, for example, adsorption or catalysis, or provides an extended surface for support of another material which has a useful chemical or physical property. Advantageously, the bodies comprise the stationary phase of a chromatographic apparatus, or of a solid phase extraction device. As used herein, the term "bodies" is generic to carbon, zeolite, alumina, silica, organic polymers or other materials in various physical or geometric forms, including particles, fibers, granules, and masses of essentially any size or shape. In the description, the term "particles" is primarily used, since this is the form most often preferred in applications of the invention to chromatographic columns and solid phase extraction devices. The bodies comprise a nucleophilic material that is reactive with silyl hydride groups of a hydrosiloxane polymer adhesive or the silyl halide groups of a halosiloxane polymer adhesive medium. The substrate has a surface composition that is preferably also nucleophilic and reactive with a hydrosiloxane or halosiloxane polymer to form a strong chemical bond.

Bonding of the nucleophilic composition of the particles, granules or other bodies to the siloxane polymer comprises a covalent bond which consists either of direct bonds between atoms of the particle and silicon atoms of the siloxane polymer or linkages that consist of an oxygen atom bonded to both an atom of the particle and a silicon atom of the siloxane polymer. It will be understood that, depending on the structure of the siloxane polymer and the exact character of the particle surface, both types of such bonds may be involved. Where the surface of the particle comprises functional groups such as halo, amino, isocyanate, isothiocyanate, sulfhydryl, etc., bonding of the particle to the siloxane polymer may comprise additional linkages resulting from reaction of such functional groups with moieties of the siloxane polymer.

According to a particularly preferred embodiment of the invention, a unique process has been discovered for the preparation of a novel composition of matter which has valuable and important properties in a wide variety of applications. A novel composition of matter comprises a siloxane polymer having adsorptive carbon or organic polymer bodies bonded to it by direct carbon to silicon bonds. Further in accordance with the invention, it has been found that the novel direct C—Si bond between an adsorptive carbon or polymer body and a siloxane polymer provides a highly advantageous means for bonding of such adsorbent particles to glass. This novel structure has further been found to provide a novel and valuable means for bonding of adsorbent carbon or polymer particles to the wall of a glass chromatographic column or the glass fibers of a solid phase extraction device.

More particularly, the preferred composition of matter of the invention comprises a structure in which the C—Si bond is contained in a moiety comprising:

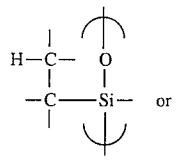 (Formula I)

or

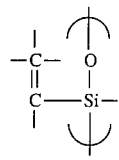 (Formula IA)

in which the carbon to carbon to silicon bond is at the surface of the carbon or polymer particle. In most instances, the hydrosilyl group may be expected to add across a double bond at the carbon surface, or across a terminal double bond or aromatic double bond of an organic polymer, to form the structure of Formula I.

A very wide variety of substituents can be attached to the free bonds of the structure of formula I. Preferably, however, the moiety of formula I has the structure:

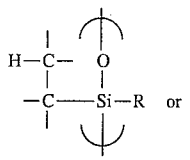 (Formula II)

or

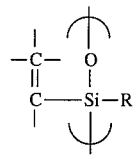 (Formula IIA)

wherein R is hydrogen, substituted or unsubstituted hydrocarbyl, alkoxy, aryloxy, nitro, cyano, amino or an —O—Si≡ moiety. Preferably, the R group is hydrocarbyl, and more preferably a $C_1$ to $C_{25}$ alkyl group, most preferably a lower alkyl group such as methyl, ethyl, propyl, isopropyl, n-butyl, amyl, hexyl, decyl or the like. R may also encompass halo-, alkoxy-, aryloxy-, amino- and cyano- substituted alkyl groups, such as for example, —$(CH_2)_xCN$, where x is 1 to 8, —$CH_2CH_2CF_3$, —$(CH_2)_x$ $CF_2)_y CF_3$, where x is 2 to 5 and y is 0 to 2, —$(CH_2)_z(CF_2)_y CF(CF_3)$ [$OCF_2CF$ $(CF_3)$]$_xF$, where z is 2 to 5, y is 0 to 2 and x is 1 to 5, and —$CH_2CH_2CH_2$ ($OCH_2CH_2)_x OR'$ where x is 0 to 5 and R' is alkyl or aryl. As a further option, R can comprise the structure

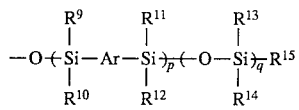 (Formula IX)

where $R^9$, $R^{10}$, $R^{11}$, $R^{12}$, $R^{13}$, $R^{14}$, and $R^{15}$ are hydrogen or hydrocarbyl, Ar is aryl and p/(p+q) is between about 0.01 and about 1.0. Primary or secondary substituted hydrocarbyl groups having a carbon chain length of greater than about 5 are preferably not used, in order to avoid undesired crosslinking reactions between siloxane polymer chains. Alternatively, R may be an aryl group, for example, a group having the structure:

 (Formula VII)

where $R^{16}$ may be alkyl, aryl, alkoxy or aryloxy having 1 to 25 carbon atoms, amino, nitro, halo or cyano. Suitable aryl groups include phenyl, or substituted phenyl such as nitrophenyl, chlorophenyl, toluyl or anilino. R and/or any of $R^1$ to $R^{16}$ may also comprise a heterocyclic group such as furyl, thienyl, pyridinyl, etc. The

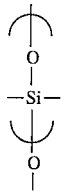 (Formula III)

group is preferably a repeating unit of an organo siloxane polymer residue which more preferably has the formula:

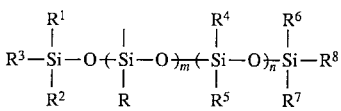 (Formula IV)

where R is as defined above and $R^1$, $R^2$, $R^3$, $R^4$, $R^5$, $R^6$, $R^7$, and $R^8$ are independently selected from among substituted and unsubstituted hydrocarbyl, nitro, cyano, and an —O—Si≡ moiety, m+n is such that the average molecular weight of the polymer is between about 80,000 and about 2 million, preferably between about 250,000 and about 500,000, and m/(m+n) is between about 0.01 and about 1.0, more preferably between about 0.01 and about 0.2. The molecular weight distribution is preferably narrow, i.e., ±5000 Daltons, as provided, for example, by chromatographic purification of a crude organosiloxane polymer. Thus, number average and weight average molecular weight are essentially the same. Where any of $R^1$, $R^2$, $R^3$, $R^4$, $R^5$, $R^5$, $R^6$, $R^7$, and/or $R^8$ is hydrocarbyl, it may be any of the groups that may constitute R in Formula II. Where any of R, $R^1$, $R^2$, $R^3$, $R^4$, $R^5$, $R^6$, $R^7$, and/or $R^8$ is —O—Si≡, it advantageously constitutes the residue of a surface silanol residue of a vitreous substrate, thus serving as a bridge between the substrate and the siloxane polymer. In this way, the adsorptive carbon or organic polymer particle may be bound to a glass or other vitreous substrate via the siloxane polymer, the polymer being bound to the carbon via the novel C—Si bond, and to the glass via one or more —Si—O—Si— bonds.

It has been found that the direct carbon to silicon (—C—Si≡) bond in the structure of Formula IV has a very high thermal stability. More particularly, it may be exposed to temperatures substantially in excess of 300° C. without breaking down.

Preferred organic polymer adsorbents useful in the compositions and constructions of the present invention include poly(divinylbenzene), copolymers of styrene and divinylbenzene, such as that comprised by the porous nonionic polymeric adsorbent material sold under the trade designation XAD# by Supelco, Inc. of Bellefonte, Pa., polystyrene, the porous highly crosslinked methacrylate copolymer resins comprised by the adsorbent material sold under the trade designation Amberchrom#, also by Supelco, acrylic ester copolymers, acrylonitrile-divinylbenzene copolymers and various polymers comprising an aromatic backbone or aromatic pendent groups. A variety of other crosslinked polymeric materials may be used, provided that they comprise a hydrocarbon moiety to which the polysiloxane may attach, preferably by a direct C—Si bond. Thus, the polymeric material of the organic polymer adsorbents is not limited to exclusively hydrocarbon polymers as long as a hydrocarbon moiety is available for reaction with the polysiloxane. Preferably, the hydrocarbon moiety includes a C=C double bond that is reactive with a hydrosilyl moiety of a hydrosiloxane polymer to produce a ≡C—Si≡ linkage of the type described hereinabove in the case of adsorbent carbon bodies. Alternatively, methylene, or pendent or terminal methyl groups of the polymer constituting the adsorbent material may react with a halosiloxane moiety of the siloxane polymer. As indicated, the organic polymer resins used as the material of adsorbent bodies are preferably substantially crosslinked. The degree of crosslinking should be sufficient to provide the desired swellability characteristics, as is well known to those skilled in the art.

Further in accordance with the invention, it has been found that bodies comprising other nucleophilic materials, such as adsorbent bodies of zeolite, alumina, and silica, may be effectively and securely bound to a glass substrate via a siloxane polymer medium. It has also been found that bodies comprising carbon, zeolite, alumina, silica, organic polymers, and other nucleophilic materials may be bound via a siloxane polymer medium to a substrate having a nucleophilic surface composition comprising metal or plastic.

A zeolite molecular sieve is typically bound to a silyl hydride polymeric adhesive via an Al—O—Si or Si—O—Si linkage. Alumina is bound through an Al—O—Si linkage; and activated silica or silica gel is bound through an Si—O—Si linkage. Each of these provides strong adherence of the adsorbent material to the siloxane adhesive. Because the siloxane also adheres strongly to the substrate material, the novel structures of the invention may be embodied in a chromatographic column or solid phase extraction device which can be contacted with a flowing matrix phase, purge gas, or rinsing solvent without dislodging the bodies of adsorbent or other material from the substrate.

A metal substrate may be bound to the siloxane polymer through a variety of linkages, depending on the nature of the metal, the natural surface film it may form, or the preliminary surface treatment to which it is subjected. Among the preferred metals for use as chromatographic column substrates are stainless steel, nickel, molybdenum and titanium. However, hydrosiloxanes and halosiloxanes readily react with essentially any nucleophile. Thus, a wide variety of metals can be used, since the surfaces of metals commonly comprise compositions of nucleophilic character. Some metals may react with silyl hydride or silyl halide moieties to form direct metal to silicon bonds. Others may react with oxides or hydroxides at the surface to bond to the siloxane through an oxygen linkage.

Plastic or resinous materials that may constitute a column wall, or the fibrous substrate of a solid phase extraction device include, for example, polyethylene, polypropylene, and poly(tetrafluoroethylene). As in the case of organic polymeric adsorbents, the polymeric material of the plastic substrate preferably comprises a hydrocarbon moiety with which a hydrosilyl or halosilyl moiety can react. Attachment of the siloxane polymer to the plastic substrate is preferably through a direct C—Si bond, as in the case of the bond between the siloxane polymer and the organic polymer of a polymeric adsorbent. In accordance with the preferred method of the invention for bonding elemental carbon to a vitreous or other substrate, the composition of Formulae I, II, and IV is prepared by reaction of a particulate carbon with an organosiloxane polymer containing silyl hydride groups and corresponding to the formula:

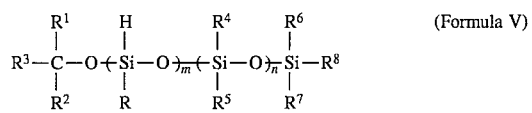

(Formula V)

where R, $R^1$ through $R^8$, m+n and m/(m+n) are generally as defined above, but at least one of $R^1$ through $R^8$ is hydrogen (or —O—Si≡). Where any of $R^1$ through $R^8$ is —O—Si≡, it may comprise a moiety of a branched organopolysiloxane, e.g., a polymer wherein R of Formula V has the structure of Formula IX, or a polymer comprising the structure:

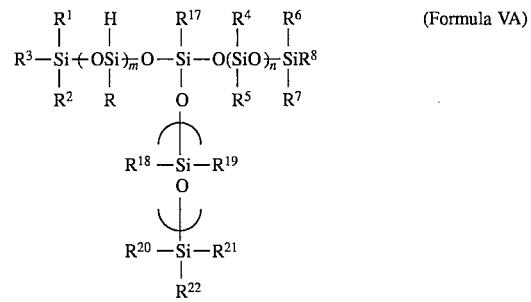

(Formula VA)

where R, $R^1$ through $R^8$ and $R^{17}$ through $R^{22}$ have the same definition as $R^1$ through $R^8$ in Formula V, m' and n' have the same definition as m and n in Formula V, and m'/(m'+n') falls within the same range as m/(m+n). Otherwise, at the start of the process of preparation, none of R or $R^1$ through $R^8$ is ordinarily —O—Si≡.

However, where the purpose is to bond carbon particles to a vitreous or other substrate, the reaction is preferably carried out in the presence of that substrate, so that hydrosilyl groups of the siloxane polymer react to bind the polymer both to the carbon particle and to the vitreous substrate. In this instance, whether the siloxane with which the carbon reacts initially contains —O—Si≡ substituents will depend on the relative rates of reaction of the polymer with the carbon and the substrate, respectively (and on whether the bond to the substrate comprises an ≡Si—O— linkage, as it typically does where the substrate is vitreous). Although we do not wish to be held to a particular theory, it is believed that hydrosilyl groups of the polymer react with residual α olefinic hydrogens of the carbon particle. Where the substrate is vitreous, hydrosilyl groups are also believed to react with residual silanol groups of the substrate. Thus, the reaction is believed to proceed according to the following scheme:

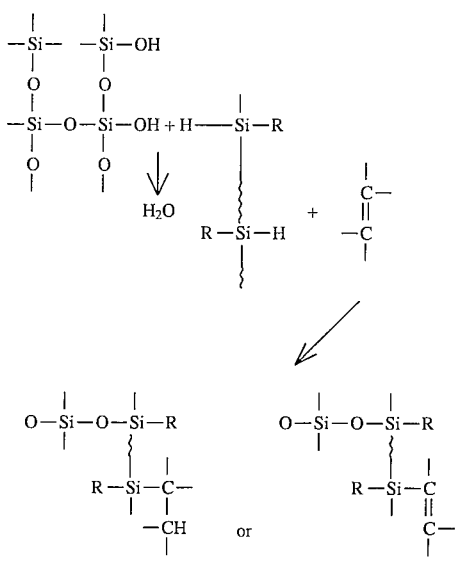

Accordingly, it is generally preferred that at least one of $R^1$ through $R^8$ be hydrogen, so that the polysiloxane has a hydrosilyl functionality of at least 2. Having such structure, the polymer can react with both carbon at the surface of the carbon particle, to provide the thermally stable ≡C—Si≡ bond, and silanol groups at the surface of the glass to provide the —Si—O—Si bond through which the polysiloxane is bound to the glass. While a hydrosilyl functionality of 2 is the minimum required for the above reaction, it is generally preferred that between about 1% and about 5% of the $R^1$ through $R^8$ substituents on the backbone silicon atoms be hydrogen. In part, the hydrosilyl functionality may be provided by dihydrosilyl groups but, in any case, it is especially preferred that m/(m+n) in Formula VI be between about 0.04 and about 0.10. Where the carbon is a carbon molecular sieve, the proportion of hydrogen substituents is optimally about 5% and m/(m+n) about 0.05. Where the carbon is graphite, the proportion of hydrogen substituent is optimally about 10% and m/(m+n) about 0.10.

Surface chemistry of the carbon particle may be complex, but the process of the invention is effective to produce direct carbon to silicon bonds between carbon of the particle and silicon of the siloxane polymer. In some instances, surface carbons of the carbon particle may be entirely bonded to other carbons, e.g., by carbon to carbon double bonds, in which case a hydrosilyl group may be expected to add across the double bond to produce the structure of Formula I. Alternatively, there may be carbon free radicals at the surface, which react directly with the hydrosilyl group to form the Si—C bond, the hydrogen either reacting with other free radicals, adding across carbon to carbon double bonds, or being released in the form of molecular hydrogen or bound to other elements. In some instances, elements such as hydrogen, oxygen or nitrogen are initially bound to some of the carbons with which the hydrosilyl group reacts. However, the molar proportion of such bound surface elements is much lower than the proportion of hydrogen in even a highly unsaturated hydrocarbon. As discussed hereinbelow, oxygen is preferably removed prior to reaction with the siloxane polymer, but quantitative removal of oxygen may not be entirely achieved. Where hydrogen, oxygen, or nitrogen are bound to the surface, the hydrosilylation reaction may cause by-product $H_2$, $H_2O$, or $NH_3$ to be released in the reaction. At the reaction temperature, these by-product gases are readily vented from the reaction system.

In accordance with the invention, essentially any of the various forms of carbon can be bonded to a siloxane polymer via direct C—Si bonds. These include for example, graphite, graphitized carbon black, turbostatic carbon, glassy carbons, and carbon in any of its other amorphous conformations, prominently including carbon molecular sieves or activated carbon molecular sieves of the type suitable for use in chromatography. Prior to reaction with the siloxane polymer, the surface of the carbon particle is prepared for the reaction by treatment to remove bound surface oxygen. Surface oxygen is removed by heating the carbon in an inert or reducing atmosphere at a temperature preferably in excess of about 225° C., more preferably above 300° C. Optionally, the carbon surface may be treated in other ways to enhance the formation of ≡C—Si≡ bonds by reaction of carbon at the particle surface with ≡Si—H groups of the siloxane polymer. For example, free radical sites may be formed on the carbon surface by treatment either with hydrogen or with a plasma, e.g., a plasma of propylene or other hydrocarbon monomer. By chemical vapor deposition, pyrolytic carbon sources such as unsaturated hydrocarbons may be deposited on the carbon surface, thereby providing —C═C— groups at the surface which can be reacted with hydrosilyl groups of the polymer.

After the carbon surface has been prepared by removal of bound oxygen, the substrate surface is contacted with a mixture of the elemental carbon and the hydrosiloxane polymer, and the mixture is heated to cause the polymer to be bonded to the carbon particles by direct carbon to silicon bonds, bonded to a vitreous substrate by reaction with surface silanol groups, or bonded to other substrates via the linkages discussed above. Preferably, the polysiloxane polymer is dissolved in an organic solvent, the carbon particles are slurried in the resulting solution, and the slurry is heated at a temperature in excess of 200° C., preferably in excess of about 250° C., to effect the —C═C—/≡Si—H reaction. The reaction can be carried out at lower temperature, for example, in the range of between about −25° and about 150° C. in the presence of a catalyst such as salts of aliphatic carbon acids. Reactions of olefins with polymethylhydrosiloxanes have been accomplished with tin hydride, platinum or rhodium catalyst; and reduction of aldehydes and ketones has been done with tributyltin, (dibutylacetoxytin) oxide, Pt/C or Pd/C). Where the reaction is carried out for attachment of carbon particles to the inside wall of a chromatographic column, the use of a catalyst is preferably avoided since the presence of residual catalyst in the resultant carbon coating may interfere with chromatographic separations. In other applications, such as solid phase extraction devices, the presence of residual catalyst may cause no particular difficulty. However, generally, it is preferred that the reaction be promoted by conducting it at elevated temperatures, above 200° C., rather than by the presence of a catalyst.

Adsorbent bodies of zeolite, organic polymer, activated alumina, activated silica, silica gel, or other nucleophilic material may be bonded to a vitreous or other substrate using substantially the same method that is used to bond carbon particles to a substrate. A hydrosiloxane polymer bonds with a zeolite molecular sieve according the reaction:

$Na_{12}[(AlO_2)_{12}(SiO_2)_{12}]$ y $H_2O$ + ≡Si—H ⟶

-continued

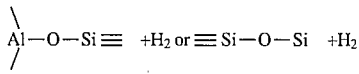

Bonding of alumina to a hydrosiloxane proceeds in the following manner:

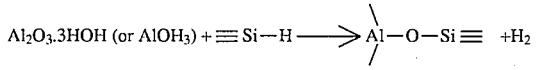

The reaction of activated silica or silica gel with a hydrosiloxane polymer proceeds as follows:

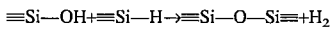

The conditions of the reaction are substantially as described above in the case of carbon particles.

To bond adsorbent particles to a substrate, the particles are preferably suspended in a solution of the polysiloxane, and the substrate is contacted with the suspension at a temperature in the aforesaid range. Essentially any organic solvent that provides effective solubilization of the organosiloxane polymers and wets the carbon particles can be used for the reaction. Among the organic solvents that may conveniently be used are alcohols such as methanol, ethanol, isopropanol and n-butanol, ketones, such as methyl ethyl ketone, methyl isobutyl ketone, and methyl isopropyl ketone, ethers such as diethyl ether, methyl ethyl ether and dipropyl ether, esters such as ethyl acetate, methyl butyrate, or amyl acetate, aromatic solvents such as benzene, toluene and xylene, halogenated solvents such as chloroform, trichloroethane, and dichloromethane, and other common solvents such as dimethylformamide, dimethyl sulfoxide, tetrahydrofuran, etc. Aprotic solvents such as carbon disulfide and acetonitrile are also useful. Preferably, the solvent used is effective to wet the carbon particles so that they are readily suspended in the polysiloxane solution. Thus, for example, where the particulate material to be bound is an amorphous carbon produced at a temperature below about 1000° C., it is typically acidic; and in this case a halogenated solvent such as dichloromethane may be preferred. For graphitic carbon, which is produced at temperatures in excess of 2500° C., tetrahydrofuran is especially preferred.

It is important to maintain the reaction mixture as substantially free of moisture. Since the solvent is the most common source of moisture, it is therefore preferred that the moisture content of the solvent be not greater than about 50 ppm, preferably not greater than about 10 ppm. Conveniently, the siloxane polymer is dissolved in the solvent with aid of agitation or exposure to ultrasound. Mechanical agitation or sonication are also preferably used to aid in obtaining a uniform dispersion of the carbon particles in the solution.

Concentrations and ratios of reactants are not narrowly critical; nor is pressure. Conveniently, the siloxane content of the solution may be between about 5 and about 100 gpl, and the concentration of carbon or other dispersed solid bodies in the pre-reaction slurry may be in the range of between about 1 and about 500 gpl, ordinarily 10 to 100 gpl. More concentrated coating solutions, in the range of 35 to 80 gpl, can be used to provide multiple layers of carbon in a single coat. Concentrations in the 10 to 30 gpl range are generally effective to provide only a single layer of carbon particles of typical size, e.g., 0.2 to 1 micron. Nonetheless, coatings having multiple layers of carbon particles can be obtained from such relative dilute compositions by applying the coating in multiple cycles.

The reactions are readily conducted at ambient pressure, but pressures ranging from a high vacuum, −29.90"Hg, to a positive pressure of up to 10,000 psi, can be tolerated without adverse effect on the reaction. When the slurry of carbon particles in siloxane solution has been brought into contact with the substrate, the solvent is removed and the siloxane reacted with the carbon particles and the substrate. The solvent may be removed in the course of heating the solution to reaction temperature. Use of vacuum or an inert purge gas may assist in solvent removal. After the solvent has been removed, the carbon/siloxane polymer mixture and the substrate surface with which the mixture is in contact are heated to a temperature in excess of about 200° C. to effect reaction between hydrosilyl groups of the polymer and surface carbon of the particle, and between hydrosilyl groups of the polymer and nucleophilic surface groups of the vitreous substrate. In the case of a vitreous substrate, the hydrosilyl groups of the siloxane polymer are reactive with silanol groups of the substrate. Where the substrate is metallic, the hydrosilyl group may react with surface oxide, hydroxide or elemental metal. Plastic substrates react in a manner similar to the organic polymers of an adsorbent body. The weight ratio of carbon to polysiloxane may vary from 1:100 to 100:1, but is conveniently between about 1:1 and about 4:1, most preferably between about 1.5:1 and about 3:1. The weight ratio of carbon to substrate is governed by the carbon loading that is required for the chromatographic or other application involved. This loading may vary widely, as discussed hereinbelow.

Either static or dynamic coating methods may used in applying a coating comprising single or multiple layers of carbon particles. In the static method, a slurry of carbon particles in a siloxane polymer solution is applied as a wet coating to the surface of the substrate, and the solvent removed by application of heat and/or vacuum. Depending on the concentration of carbon particles and the viscosity of the solution, a coating of up to six carbon particles in thickness may be obtained in a single coating cycle. According to the dynamic method, the slurry is forced from a reservoir through a tubular column under inert gas pressure. A slug of the slurry moves ahead of the gas phase, leaving behind a film adhering to the interior column wall. As the slug moves forward, an annular transition segment of the slurry, having a roughly conical inside surface, moves along the wall behind the slug intermediate, the slug, and the wet, stable cylindrical film that is deposited on the wall. The thickness of the stable film is a function of the angle between the wall and the interior conical surface of this transition segment. It has been found that thicker films are associated with both high carbon concentration in the slurry and a relatively steep angle between the slug and the substrate, i.e., both the advancing angle at which the front face of the slug meets the substrate, and the trailing angle between the transition segment and the substrate; and further that the steepness of these angles varies directly with the gas pressure. For example, a coating having a thickness of as many as three carbon particles of 0.5 micron diameter may be produced in a single pass on the inside wall of a glass column having an I.D. of 0.53 mm, by application of a slurry having a carbon concentration of between about 30 and about 50 gpl under nitrogen or helium pressure of 20 psi or more. By way of further example, if a slurry having such concentration, and a volume approximately one third that of the interior portion of the column, is provided in a reservoir, and the entire contents of the reservoir forced through the column at a pressure of 15 psig, approximately one half of the volume of the slurry originally provided in the reservoir remains as a wet coating on the interior column wall. As in the case of the static coating method, solvent is removed by application of heat and/or vacuum. In the dynamic method, the inert gas may conveniently serve as a carrier gas for assisting removal of solvent. In both the static and dynamic method, the reaction between the siloxane and both the carbon and the substrate is effected by postheating to a temperature in the range noted above.

The bonding medium of the invention provides a highly stable bond between the inside wall of a glass, metal or plastic chromatographic column and a stationary phase adsorptive medium comprising carbon of very fine particle size, e.g., between about 0.1 and about 100 µM having a surface area of between about 1 and about 3000 m$^2$/g. More particularly, columns can be constructed using graphitic carbon having a B.E.T. surface area in the range of about 2 to about 100 m$^2$/g, or from carbon molecular sieves having B.E.T. surface areas in the range of between about 500 and about 1300 m$^2$/g. Particularly preferred carbon molecular sieves have a particle size of between about 0.2 and about 2 µM, a total pore volume of between about 0.1 and about 3 cc/g, a macropore (diameter >500 Å) volume of between about 0.1 and about 2.0 cc/g, a mesopore (diameter between 20 and 50 Å) of between about 0.1 and about 2.0 cc/g, and a micropore (diameter 3 to 20 Å) of between about 0.1 and about 2.0 cc/g. Graphitic carbons are generally non-porous and present an external surface area in the range of 1 to 100 m$^2$/g. However, a useful graphitized carbon sold by Supelco under the trade designation Carbopack Y has a B.E.T. surface area of about 250 m$^2$/g and comprises a modest level of microporosity, less than about 0.5 cc/g. PLOT columns having an adsorptive surface comprising such carbon adsorbents may be of very small diameter, in the capillary range, yet present a very high adsorptive surface area per unit of column length, and be subject to operation at very low pressure drop. Thus, for a service in which a packed column would need to be operated at a pressure of 40,000 psi, the coated wall capillary type chromatographic column of the invention can be operated at a pressure of only 4 psi.

Absorbent bodies comprised of zeolite, alumina, organic polymers, or other nucleophilic material may be adhered to a vitreous, metal, plastic or other nucleophilic substrate by the medium of a hydrosiloxane polymer. The method is essentially as described above, except that zeolite, silica, and aluminum are not deoxidized prior to the bonding reaction. Nor is it necessary or appropriate to attempt to deoxidize an organic polymer. In any event, the adsorbent bodies are slurried in a hydrosiloxane polymer of the same character as that described above, and in the same range of concentrations and the slurry is applied to the substrate and reacted under substantially the same conditions as those described above. Where the adsorbent material or the substrate is comprised of an organic polymer, the temperature should be controlled in a range which will not adversely affect the dimensional stability and/or mechanical properties of the polymer or, in the case of a porous polymer adsorbent material, adversely affect the porosity or B.E.T. surface area of the adsorbent bodies. The temperature limits of such materials are well known to the art and easily accessible through standard literature. Thus, those skilled in the art will be aware of the temperature limitations that may apply to any particular polymeric material. Where the temperature must be controlled at a relatively low level, the reaction is carried out satisfactorily by allowing additional reaction time. For example, a polyethylene or polypropylene substrate may be bonded to a polysiloxane polymer at a temperature in the range of between about 100° C. and about 150° C.

Adsorbent bodies of zeolite molecular sieves typically have a particle size of between about 0.1 and about 5 microns, an average pore volume in the range of between about 0.3 and about 0.7 cc/g, and an average pore size in the range of about 5 Angstroms. The B.E.T. surface area of zeolite molecular sieves is generally in the range of about 300 to about 400 m$^2$/g.

Adsorbent bodies of activated alumina are generally in the submicron particle size range, i.e., between about 0.1 and about 5 µ. Activated alumina has an average pore size in the range of about 0–100,000 Angstroms, a pore volume of between about 0.25 and about 1 cc/g, and a B.E.T. surface area in the range of about 300 to about 400 m$^2$/g.

Activated silica adsorbent bodies have a particle size of between about 1 and about 10, µ an average pore size of between about 0 and about 1000 Å, and a pore volume of between about 0.5 and about 20 cc/g. Silica gel has an average pore size in the range of between about 3 and about 500 Å, and an average pore volume in the range of between about 0.5 and about 20 cc/g, and is available in a typical particle size of between about 1 and about 1,000. B.E.T. surface area is in the range of between about 20 and about 400 m$^2$/g in the case of activated silica, and between about 50 and about 1300 m$^2$/g in the case of silica gel.

Porous organic polymers produced by emulsion polymerization may be monodisperse (with respect to particle size), i.e., narrowly distributed within a particle size range of between about 1 and about 2 microns. Such porous polymer bodies exhibit very wide range of B.E.T. surface areas, e.g., from 1 to about 1300 m$^2$/g, commonly 500 to 900, most typically 700 to 800 m$^2$/g. Pore sizes are in the range of between about 100 and about 200 Angstroms. Pore volume is generally in the range of between about 0.2 and about 0.2 cc/g.

Although porous adsorbent materials are preferred for many applications, the adsorbent bodies of the structures of the invention may also be constituted of substantially non-porous carbon, organic polymer and other nucleophilic materials.

Schematically illustrated in FIG. 2 is a transverse cross section of a chromatographic column of the invention. An actual photomicrograph of a segment of this cross section is shown in FIG. 1. Bound to and extending along interior wall 3 of a tubular glass column 1 is coating layer 5 which comprises a network or webbing of polysiloxane 7 having carbon particles 9 embedded therein. As contained by the polysiloxane network, the carbon particles are effectively stacked inward of wall 3 in a plurality of layers which may in total thickness range from about 0.2 microns to about 1.0 mm, equivalent to as many as fifty effective layers of carbon. Carbon particles are distributed within network 7 both laterally and vertically with respect to the surface of wall 3. The —Si—O—Si— bonds between the polysiloxane webbing and the glass wall, and the ≡C—Si≡ bonds between the webbing and the carbon are stable at temperatures up to and above 400° C. Moreover, the mechanical strength of the bonds prevents carbon from being loosened and entrained in either a sample matrix or a rinsing fluid. Yet despite the high integrity of the bonding medium, coating layer 5 is readily permeable to analytes contained in a sample matrix, so that the carbon surfaces throughout the coating layer are accessible to the analytes. It is believed that coating layer 5 comprises a substantial degree of porosity, the pores providing tortuous paths for the analyte to transfer from particle to particle, hence differential adsorption is accomplished. It is further understood that the polysiloxane webbing is permeable to Knudsen diffusion of analytes, further augmenting access of analytes to the carbon surfaces. In any case, the carbon coating presents a very high adsorptive capacity, and provides a very high degree of resolution per unit of column length.

It will be understood that, as used herein, the term "chromatographic column" does not necessarily denote a vertical column, but encompasses any tube, duct or chamber containing sorbent material over which a sample matrix may be passed for purposes of chromatographic separation.

Glass, metal or plastic chromatographic columns of the invention, having active carbon coated on the interior walls, may be used in gas/solid chromatography for separating complex sample matrices. The choice of carbon is dependent on the nature of sample. Carbon molecular sieves separate analytes based on molecular size, while other carbon adsorbents effect separation based on differences in electronic activity among the analytes. Optionally, selectivities can be substantially enhanced by coating the carbon particles with liquid stationary phase materials on which the relative adsorptivities of analytes, particularly based on their electronic activities, vary more sharply than on the carbon itself. The column of the invention allows such gas/liquid/solid chromatography to be conducted with high capacity, minimal axial backmixing, and low pressure drop. Particularly advantageous liquid stationary phase materials are cyclodextrins, which can readily be coated onto the surface of the bound carbon particles. Alternatively gas/liquid or gas/liquid/solid chromatography can be conducted using a phthalocyanine, or other polar, stationary phase, coated on a carbon support that is bonded to the interior column wall in accordance with the novel compositional structure of the invention. By varying the layers of liquid phase coated over the carbon, the column function can be varied from entirely gas/liquid chromatography to varying degrees of gas/liquid/solid operation. With greater than about five layers of liquid, the gas adsorptive capability of the carbon is essentially completely masked, and the column functions in a liquid/liquid mode. As the number of layers decreases below five, influence of the carbon progressively increases. Although the cyclodextrin or phthalocyanine is bound to the carbon only by Van der Waals forces, strong bonding of the carbon to the glass or other column wall surface via the polysiloxane prevents both the carbon and the liquid phase it supports from being swept out of the column by a flowing gas sample matrix, even when multiple liquid layers are used. It will be understood that by substitution of a liquid mobile phase, columns constructed according to the invention can be operated in a liquid/liquid mode as well, and that the strong bond between the carbon support and the glass surface prevents entrainment of carbon in the liquid mobile phase.

Columns of the invention coated with zeolite molecular sieve, activated alumina, activated silica, silica gel and adsorbent organic polymers via a polysiloxane adhesive also may be advantageously used in gas/solid chromatography applications. Separations are primarily effected on a size exclusion principle, but other mechanisms of differential adsorption may be implemented in such columns. As in the case of carbon, adsorbent bodies comprising silica, alumina, zeolite, organic polymer and other adsorbent materials may function as supports for a stationary liquid phase in reversed phase gas/liquid or liquid/liquid chromatography. The liquid phase may be adhered to the surface of the adsorbent body by Van der Waals forces only or, alternatively, the support may be derivatized by having materials chemically bonded thereto which present a stationary liquid surface for contact with a mobile liquid or gas phase. Thus, for example, silica that is bonded to a glass or metal substrate via a polysiloxane polymer, may be derivatized by attachment of aliphatic moieties thereto, such as octadecyl radicals.

In accordance with the chromatographic method of the invention, a sample matrix mobile phase containing one or more analytes is passed through a coated wall column of metal, plastic or vitreous material. A preferred substrate material is silica glass. The walls of the column are coated with adsorbent carbon, zeolite, alumina, silica, or organic polymer, which is bound to the substrate via a polysiloxane polymer, in the manner described hereinabove. Preferably, the column is of capillary diameter, i.e., typically between about 0.1 and about 1 mm. Thus, the chromatographic column of the invention is adapted for use in PLOT, SCOT, CLOT or GLOT form. Columns of capillary diameter may contain a carbon coating of small enough particle size and high enough loading to present an adsorptive area of between about 1 and about 12 $m^2$ per m of column length, or between about 600 and about 7250 $cm^2$ per $cm^2$ of internal wall surface, for a column internally coated with a single carbon layer. For other adsorptive materials, the ranges of adsorptive area are as set forth in Table 1.

TABLE 1

| Adsorbent Mat'l | B.E.T. Surface Area per | |
| --- | --- | --- |
|  | Unit col. length $m^2/m$ | Unit col. Area $cm^2/cm^2$ |
| Zeolite | 1–10 | 500–10,000 |
| Alumina | 1–40 | 300–10,000 |
| Silica | 1–12 | 300–10,000 |
| Org. Polymer | 1–12 | 300–10,000 |

By use of multiple coatings, the absorptive capacity can be substantially increased without significant increase in pressure drop. For example, a column having fifty C/siloxane layers on the internal wall may present an adsorptive area of between about 1 and about 600 $m^2$ per m of column length, or between about 600 and about 375,000 $cm^2$ per $cm^2$ of internal wall surface. Such adsorptive area is provided, for example, by carbon having a particle size of between about 0.05 and about 10 µM, and a B.E.T. surface area of between about 1 and about 1500 $m^2/g$, at coating thickness of between about 0.05 and about 1 mm and a loading of between about 0.001 and about 0.600 $g/cm^2$ of internal wall surface. Typically the total weight of carbon in a capillary column is in the range of between about 1.0 mg and about 10 g.

In the case of a zeolite molecular sieve having a particle size between about 0.5 and about 10 microns, B.E.T. surface area of between about 200 and about 800 $m^2/g$, a coating thickness of between about 0.5 and about 500 µm and a loading of between about 0.001 and about 1.0 $g/cm^2$, a column having fifty zeolite/siloxane layers on the internal wall of a column may present an adsorptive area of between about 1 and about 400 $m^2$ per m of column length, or between about 500 and about 10,000 $cm^2$ per $cm^2$ of internal wall surface. For fifty layers of other adsorbent bodies embedded in a polysiloxane, the comparable ranges for:

(a) alumina are a particle size between about 0.5 and about 10 microns, a B.E.T. surface area of between about 200 and about 800 $m^2/g$, a coating thickness of between about 0.5 and about 500 µm and a loading of between about 0.001 and about 1.0 $g/cm^2$, to provide an adsorptive area of between about 1 and about 10 $m^2$ per m of column length, or between about 300 and about 300,000 cm² per cm² of internal wall surface;

(b) for activated silica are a particular size between about 0.5 and about 10 microns, a B.E.T. surface area of between about 5.0 and about 1000 m²/g, a coating thickness of between about 0.5 and about 500 μm and a loading of between about 0.001 and about 0.6 g/cm², to provide an adsorptive area of between about 1 and about 12 m² per m of column length, or between about 500 and about 10,000 cm² per cm² of internal wall surface;

(c) for silica gel are a particle size between about 0.5 and about 10 microns a B.E.T. surface area of between about 5 and about 1200 m²/g, a coating thickness of between about 0.5 and about 500 μm and a loading of between about 0.001 and about 0.6 g/cm², to provide an adsorptive area of between about 1 and about 12 m² per m of column length, or between about 600 and about 7250 cm² per cm² of internal wall surface;

(d) for a styrene-divinylbenzene copolymer are a particle size between about 1 and about 10 microns, a B.E.T. surface area of between about 1 and about 1200 m²/g, a coating thickness of between about 0.5 and about 500 μm and a loading of between about 0.001 and about 10 g/cm², to provide an adsorptive area of between about 1 and about 12 m² per m of column length, or between about 600 and about 7250 cm² per cm² of internal wall surface; and (e) for a polymethacrylate ester polymer are a particle size between about 1 and about 10 microns, a B.E.T. surface area of between about 1 and about 1200 m²/g, a coating thickness of between about 0.5 and about 500 μm and a loading of between about 0.001 and about 12 g/cm², to provide an adsorptive area of between about 1 and about 12 m² per m of column length, or between about 500 and about 7250 cm² per cm² of internal wall surface.

In each case, the total weight of adsorbent bodies on the wall of a capillary column is comparable to that noted above in the case of carbon, i.e., roughly about 0.1 to about 10 g.

Chromatographic columns of the invention can be used in chromatographic analyses, or other chromatographic separations, of an essentially unlimited variety of mixtures. According to the chromatographic process of the invention, a mixture to be analyzed or otherwise separated is introduced into the column, and components of the mixture are eluted from the column using a liquid solvent or carrier gas. It is particularly preferred that the column be an open column such as the PLOT, SCOT, CLOT or GLOT columns described hereinabove. In gas chromatography, the column of the invention has been demonstrated to be suitable for such exemplary applications as the separation of: various hydrocarbon gases; combustion gases; aqueous solutions of nonionic solutes; and light sulfur gases. It is particularly effective for use in separation and analysis of flue gases obtained from the combustion of sulfur-bearing fuels, and light sulfur gases of the type that may be released from crude petroleum or sour petroleum fractions. Advantageous applications particularly include the separation and analysis of mixtures comprising sulfur bearing carbon compounds having boiling points below about 22° C. at atmospheric pressure. The chromatographic columns of the invention are further suited for separation and analysis of internal combustion engine exhaust gases and other gases which may contain significant fractions of oxides of nitrogen, oxides of sulfur, or both. The conditions for conducting these and other analyses and separations are not narrowly critical.

However, the separation mechanism of porous carbon, zeolite, alumina, silica or organic polymer PLOT columns is typically one of molecular size and shape, and in some parallel instances becomes one of boiling point of the introduced analytes. For these reasons, the porosity and/or specific surface area of the adsorbent body may play a major role in the separation characteristics of such PLOT columns. More particularly, the particulate carbon used in a size exclusion PLOT column preferably has a pore volume of about 1.5 to about 2.0 cc/g and a B.E.T. surface area of between about 400 and about 1300 m²/g, preferably between about 700 and about 800 m²/g. Comparable parameters for other adsorbent materials are set forth in Table 2.

TABLE 2

Preferred Characteristics of Adsorbent Materials Used for Size Exclusion Separation - PLOT Column

| Adsorbent Material | Pore Vol. | B.E.T. Area | Preferred B.E.T. area |
|---|---|---|---|
| Zeolite | 0.40 | 350 | 350 |
| Alumina | 0.45 | 250 | 200 |
| Act. silica | 1.50 | 300 | 350 |
| Silica gel | 1.50 | 500 | 7000 |
| DVB | 1.25 | 350 | 750 |
| Polymethacrylate | 0.20 | 250 | 500 |

In other applications, such as, for example, the separation of complex environmental mixtures such as chlorinated compounds present in drinking water, waste effluent streams, and hazardous waste sites, relatively low porosity graphitic carbons may be used. Graphitic carbons can also be used in analyses of halofluorocarbons ("Freons") typically used in refrigerant systems. Substantially non-porous carbons useful in certain of these applications have a B.E.T. surface area generally less than 100 m2/g, while slightly porous graphitic carbons generally have a B.E.T. surface area in the range of about 250 m²/g and about 500 m²/g.

Using open columns of the type described above, the separation process can be operated at very modest pressure drop, e.g., in the range of 0.1 to 100 psi, more commonly in the range of between about 2 and about 30 psi. Exemplary conditions are illustrated in the working examples set forth hereinbelow. Acceptable variations in these conditions will be readily apparent to those skilled in the art.

Columns that are interiorly coated with carbon or other adsorbent particles in accordance with the invention can be used in sample preparation applications also. When sample matrices contain impurities which are not to be analyzed, but whose presence can interfere with the determination of analytes of interest, it is desirable or necessary to remove the impurities before chromatographic analysis is begun. One way in which impurities may be removed is to cause the sample to flow through a column containing an adsorptive material which has a stronger affinity for the impurities than for the analytes. Carbon molecular sieves, porous carbons, activated porous carbons, zeolites, activated alumina, silica, silica gel, and porous organic polymers are especially suitable for this purpose. By use of a coated wall column of the invention for sample preparation, the sample may be processed rapidly, with low pressure drop, and with high selectivity so that impurities are quantitatively removed while the loss of analyte during sample preparation is carefully and reliably avoided.

Illustrated in FIG. 3 is a solid phase extraction device which comprises a syringe barrel 101 containing a coated glass fiber 103 which can be exposed for immersion in a sample matrix by moving it out of the barrel through a septum 105 in exit port 107 of the barrel. The inner end of fiber 103 connects to a plunger 109 via a screw hub 111. Plunger 105 is telescoped within barrel 101 at the end of the barrel opposite port 107, for slideable axial movement relative to the barrel while in sealing engagement with the interior wall thereof. A ferrule 113 attached to the end of the barrel surrounding port 107 holds a septum piercing hollow needle 115. Needle 115 is aligned with fiber 103 so that the fiber may be passed axially through the interior of the needle. Thus, by pressing down on the plunger, the fiber may be moved axially of the barrel and out through septum 105 and needle 115, for immersion into a sample matrix and adsorption of an analyte, or contaminant, or component contained within the matrix. After the adsorption of such component, fiber 103 is conveniently withdrawn back into the barrel until such time as the adsorbed component is to be desorbed into another matrix, for example, into the mobile phase of a chromatographic separation system. By then depressing the plunger the fiber 103 may be forced out of the barrel and into a sample matrix, or into the injection port of a chromatographic column.

Fiber 103 is coated with fine particles 117 of carbon or other adsorbent material which are bound to the glass surface via siloxane polymers in the manner described hereinabove. FIG. 4 shows a cross section of one of the fibers of the solid phase extraction device of FIG. 3. From FIG. 4 it may be seen that the adsorbent particles are embedded in a network or webbing 119 of polysiloxane on the outside of the fiber and extending along thereof. This webbing is comparable to the webbing 7 of polysiloxane on the inside surface of the tubular wall of the chromatographic column illustrated in FIGS. 1 and 2. The single fiber 103 having a length, for example, of 0.1 m, may comprise an active surface area of between about 1 and about 1.2 $m^2$, using adsorbent bodies having the B.E.T. surface area discussed hereinabove.

When the device of FIGS. 3 and 4 is immersed in a sample matrix, analytes or impurities having an affinity for the carbon are adsorbed thereon, and thus removed from the sample matrix. In this manner, for example, impurities may be removed from a matrix, which then may be subjected to chromatography or other analysis. Alternatively, analytes of interest may be removed from the sample matrix, then transferred from the carbon or other adsorbent particle surface to another sample matrix, free of impurities that may contaminate the first matrix. If desired a more concentrated sample solution may be prepared in this fashion, using a much lower volume of eluting solvent than would be required in a column type extraction device, and orders of magnitude less solvent than would be required using conventional liquid/liquid extraction techniques. Access of analyte to the carbon or other adsorbent particles embedded in webbing 119 is realized in essentially the same manner as in the case of the webbing 7 of the chromatographic column of FIG. 1. Samples of analytes that have been concentrated or purified by solid phase extraction may then be subjected to further analysis by chromatography or other means.

The novel structures of the invention may be embodied in other forms of separation devices. For example, the adsorbent bodies may be adhered via a siloxane polymer to the fibers of a woven or blown fiber fabric. Conveniently, such fabric may be cut or formed in the shape of a disk, through which a matrix solvent containing analytes to be removed are passed orthogonally to the surface of the fabric. If desired, a solid phase extraction device may comprise a multiplicity of layers of such fabrics, e.g., in the form of stacked disks as shown in U.S. Pat. No. 5,279,742, the disclosure of which is incorporated herein by reference. In such a device, the matrix solution is passed sequentially through the stacked disks of fabric, which may each contain the same adsorbent material, or which may contain different adsorbent materials that are effective for adsorption of different analytes. The latter arrangement may be advantageously used for separation of a plurality of analytes in the sample by physical separation and separate elution of the disks. However, it should be noted that a particular advantage of the novel structures of the invention arises from the strong adsorptive power and large adsorptive capacity made possible by the secure adherence of a high concentration of adsorbent bodies to a fiber substrate. Thus, unlike certain of the stacked disk systems of the prior art, multiple fabric layers are not usually necessary to effect separation of a single analyte. Nonetheless, the stacked disk arrangement may be effectively used in the manner described herein for definitive and quantitative separation of different analytes.

In preparation of the adsorbent filter of the invention, a solution of siloxane polymer is prepared in a suitable solvent, and the adsorbent particles suspended in the resultant solution, in the manner essentially as described above. The suspension is drawn into a graduated/calibrated pipette and then discharged from the pipette over the top of a fiber filter to provide an even coating over the filter. The filter is thereafter placed in a vacuum-drying oven and dried under vacuum or inert gas at a temperature in the range described above as effective for reaction of the hydrosiloxane polymer with the nucleophilic composition of the adsorbent particles, generally >150° C. If the filter walls or fibers are of a plastic material such as polypropylene or polyethylene, drying and reaction of the polysiloxane with the substrate and the adsorbent bodies is preferably conducted at a temperature between about 100° C. and about 150° C.

The structures of the invention are also useful in a variety of other differential adsorption separation devices. For example, illustrated in FIG. 9 is a denuder device that is useful in removing contaminants from an air sample. The denuder comprises a glass, plastic or metal tube 201 having adsorbent particles 203, typically of carbon or MgO, bound to the interior wall 205 of the tube via a polysiloxane polymer medium 207. A gas sample enters the tube through an inlet nipple 209, and exits through an exit nipple 211. In an alternative structure as illustrated in FIG. 10, the denuder comprises a plurality of parallel tubes 301 secured in tube sheets 311 and 313, and having adsorbent particles 303 bound to the interior walls 305 of the tubes via polysiloxane. Sample gas enters the tubes through an inlet head 307 and exits the tubes via a discharge head 309. The structure of FIG. 10 provides an enhanced adsorptive surface area as compared to the denuder of FIG. 9.

Such devices may be used upstream of a glass or Teflon fiber filter used to collect particulates from an air sample in a determination of particulate concentration. For example, nitric acid in the air may be removed by adsorption on the carbon or MgO, thus eliminating an artifact that may otherwise be encountered in the analysis of the air sample for nitrate-bearing particulates. The denuder of the invention may be advantageously used, for example, in the method and apparatus described in Shaw, et al., "Measurements of Atmospheric Nitrate and Nitric Acid; the Denuder Difference Experiment," *Atmospheric Environment*, Vol 16, No. 4, pp. 845–853 (1962); and in Stevens and Dzubay, "Sampling of Atmospheric Sulfates and Related Species," *Atmospheric Environment*, Vol. 12, pp. 55–68 describes another denuder apparatus and application thereof.

It has further been found that the structure of the invention may be usefully embodied in a catalytic reactor in which a catalyst is bonded to a wall of the reactor via a polysiloxane adhesive. Essentially any metal or ceramic wall having a nucleophilic surface composition may be used as the substrate for the polysiloxane bound catalyst. The catalyst may be any catalyst having a surface composition sufficiently nucleophilic for reaction with silyl hydride moieties of the siloxane polymer.

Although it is preferred for many applications to adhere the bodies of nucleophilic material to the substrate by bonding through the silyl hydride groups of a hydrosiloxane polymer, it has been found that, in the alternative, the bonding reaction with the polysiloxane may be effected through the silyl halide functionality of a halosiloxane polymer. Substrate materials may also react with a silyl halide rather than a silyl hydride. Where the material of the substrate or particulate material is a glass, metal, alumina, silica, zeolite, or the like, the bond between that material and siloxane is via an oxygen linkage, e.g., Si—O—Si, Si—O—Al, or Si—O—M (where M=metal), regardless of whether that material reacts with a silyl hydride or silyl halide group. Carbon and organic polymers react with either a silyl hydride or silyl halide to produce a direct ≡C—Si≡ bond.

In bonding bodies of nucleophilic composition to the surface of a vitreous or other substrate, the substrate surface is contacted with a mixture of the halosiloxane polymer, and a granular or particulate zeolite, alumina, silica, organic polymer, elemental carbon or other nucleophilic material, and the mixture heated to cause the siloxane polymer to be bonded to the particles by and to the substrate. To carry out this process, the halosiloxane polymer is preferably dissolved in a suitable solvent, the granular or particulate slurried in the solution, and the substrate contacted with the slurry and heated to effect the reaction. The halosiloxane polymer has the structure:

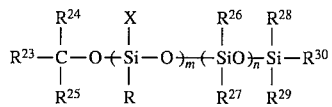

where X is halogen R, $R^{23}$, $R^{24}$, $R^{25}$, $R^{26}$, $R^{27}$, $R^{28}$, $R^{29}$ and $R^{30}$ are independently selected from among substituted and unsubstituted hydrocarbyl, nitro, cyano, halo and an —O—Si≡ moiety, m+n is such that the molecular weight of the polymer is between about 80,000 and about 2 million, and m/(m+n) is between about 0.01 and about 1.0, more preferably between about 0.02 and about 0.2. Where any of R, $R^{23}$, $R^{24}$, $R^{25}$, $R^{26}$, $R^{27}$, $R^{28}$, $R^{29}$ and $R^{30}$ is hydrocarbyl, it may be any of the groups that may constitute R in Formula II. Where any of R, $R^{23}$, $R^{24}$, $R^{25}$, $R^{26}$, $R^{27}$, $R^{28}$, $R^{29}$ and $R^{30}$ is —O—Si≡, it advantageously constitutes the residue of a surface silanol residue of a vitreous substrate, thus serving as a bridge between the substrate and the siloxane polymer. Alternatively, a branched polysiloxane may be used, comparable to the type represented by Formula VA or Formula V wherein R comprises Formula IX, but containing a halogen substituent in place of the hydrogen substituent at the point of reaction between the siloxane and the carbon surface.

Although carbon bodies are preferably deoxygenated prior to reaction with either a hydrosiloxane or halosiloxane polymer, carbon bodies having surface ≡C—OH functionality may also be used, in which case the attachment is via a ≡C—O—Si≡ linkage. In the latter instance, the composition of the bonding means corresponds to the formula:

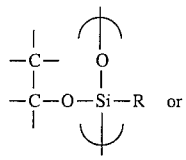

(Formula VIII)

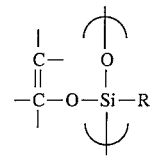

(Formula VIIIA)

where R is as defined above. Although its thermal stability is not as great as that of the direct C—Si bond, the C—O—Si bond nonetheless comprises a means for bonding the carbon particles to the glass whose integrity is substantially superior to that of the Van der Waals type bonding agents that have been conventionally used in the art. In this embodiment of the invention, a siloxane polymer comprising a silyl hydride and/or silyl halide functionality is reacted with carbon particles having residual bound oxygen or hydroxyl groups on the surface thereof:

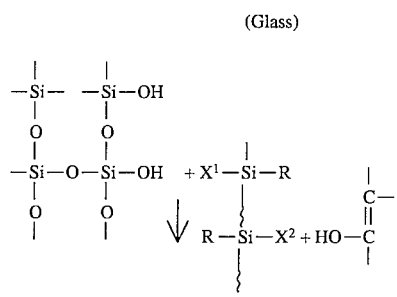

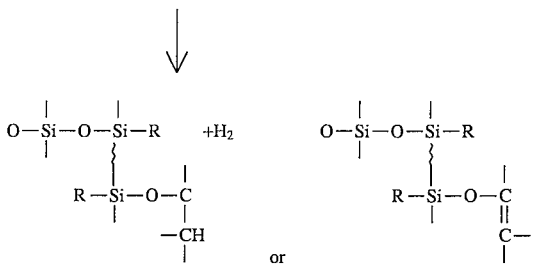

where each of $X^1$ and $X^2$ is either hydrogen or halogen.

For purposes of this reaction, a carbon surface is advantageously prepared to introduce bound oxygen or hydroxyl groups. This may be effected, for example, by contacting the surface with an oxidizing agent such as nitric acid or an oxidizing plasma, e.g., a plasma comprising an oxidized organic monomer such as benzylic acid.

It will be understood that the siloxane polymer may comprise both silyl hydride and silyl halide, typically silyl chloride or silyl bromide, functionality, and that the substrate may react with one functional group, the particulate, granular or fibrous bodies may react with the other functional group, or both functionalities may react with both substrate and the discrete bodies. The discrete bodies may serve any of a large variety of functions. As noted, they may constitute the adsorbent bodies of a chromatographic column or solid phase extraction apparatus, or they may comprise a solid phase catalyst bound to the wall of a tubular reactor. In chromatographic, solid phase extraction and catalytic applications, the bodies are ordinarily comprised of adsorbent material. In many but not all instances, the adsorbent material is porous, preferably comprising a high degree of porosity and a substantial B.E.T. surface area as described above.

Where the invention is embodied in a chromatographic apparatus or solid phase adsorption device, discrete adsorbent bodies are typically bonded to a monolithic or essentially monolithic substrate, such as an interior wall of a chromatographic column, or a fiber or contiguous network of fibers that support the adsorbent particles of a solid phase adsorption device. As used herein, the term "monolithic" includes essentially monolithic structures such as a weave or mat of contiguous fibers.

In certain applications known to the art, a particulate substrate may provide desirable functions or advantages. It will be understood that, in certain embodiments, the novel chromatographic apparatus or solid phase adsorption device of the invention may comprise a substrate which itself comprises discrete bodies, to which discrete adsorbent bodies are bonded with a siloxane polymer. There may also be applications other than in chromatography, sample preparation, or catalysis wherein discrete bodies having a functional surface property are bonded to a monolithic or particulate substrate via the medium of a siloxane polymer.

While the emphasis of the above disclosure has been on discrete bodies which are adsorbent, or preferably porous, it will be understood that the compositions and structures of the invention are further applicable to the bonding to substrates of other bodies of nucleophilic material that may be non-porous and/or non-adsorbent and/or not discrete. In the field of chromatography for example, a plug of fibrous material, such as rock wool, may be adhered to the interior wall of a column via a siloxane polymer to provide support for a packed bed of particulate or granular adsorbent material that comprises the stationary phase of a chromatographic system.

To produce a packed column in which the packing is secured by rock wool end plugs, a plug is force fit into the one end of the column and packing introduced. If plug is used at the other end of the column, it is force fit into that end after the packing is in place. Thereafter, a solution of a siloxane polymer, preferably a hydrosiloxane polymer, in a suitable solvent (such as dichloromethane) is dispensed into each end of the column that contains a wool plug. The column ends are then inserted into a suitable heating device to effect bonding of the silyl hydride (or silyl halide) functionality of the siloxane polymer to the interior wall of the column. The temperatures required for the reaction are as discussed above.

The following examples illustrate the invention.

EXAMPLE 1

Dichloromethane (2.0 mL) was mixed with a polymethylhydro-dimethyl siloxane glue having a molecular weight of 210,000 Daltons, in which 5% of $R^1$ to $R^9$ are hydrogen, the remainder of $R^1$ to $R^9$ are methyl, and m/(m+n) is 0.05 (80 mg), and the resulting mixture was sonicated for approximately 1.0 hours to dissolve the siloxane in the solvent. Particulate carbon (120 mg) sold under the trade designation Carboxen 1006 by Supelco, Inc. was weighed out into a separate vial, and the solution of siloxane in dichloromethane added to the vial containing the carbon. Carboxen 1006 has a particle size of 0.4 to 0.5 μM, a B.E.T. surface area of 750 $m^2$/g, a total pore volume of 1.5 cc/g, a macropore volume of 0.5 cc/g, a mesopore volume of 0.5 cc/g a micropore volume of 0.5 cc/g and a density of 0.44 g/cc. The resulting slurry was sonicated for 2.0 hours to uniformly suspend the carbon in the solution. The sonicated slurry was then transferred to a reservoir for use in providing a porous layer coating on the inside wall of a tubular fused silica column having an I.D. of 0.53 mm and a length of 30 meters.

A flow of $N_2$ was established in the column at a pressure of approximately 20 psig and the slurry of carbon in siloxane solution flowed by gravity and $N_2$ pressure through the column from the reservoir. The suspension was allowed to pass entirely through the column, providing a coating of carbon in siloxane on the internal glass wall. Effluent siloxane suspension was collected in a dispensing vial. After drainage of the effluent had substantially ceased, the column was placed in an oven, and heated at 260° C. for about 10 minutes under a $N_2$ purge at a pressure of about 5 psig. Reaction of the siloxane polymer with both the carbon and the glass resulted in a carbon coating on the interior surface of the column which was strongly bonded to the fused silica glass via a webbing of the siloxane.

This procedure was repeated multiple times to provide a column having multiple layers of carbon bound to and embedded in a porous siloxane polymer webbing that was in turn bonded to the glass. A photomicrograph of a cross-section of the resulting column is set forth in FIG. 1.

EXAMPLE 2

Using the column prepared in the manner described in Example 1, a mixture of gas containing carbon monoxide, carbon dioxide, methane, ethane, ethylene, and acetylene in bulk nitrogen was subjected to chromatographic separation. The sample was injected at the column inlet and caused to flow through the column by a mobile phase comprising helium. The helium eluent was passed through the column at a flow rate of 3.00 mL/min. During elution, the column temperature was initially maintained at 35° C. for three minutes, then ramped up to 225° C. at a heating rate of 24° C. per minute. Column pressure was initially 4 psig, increasing to 6 psig at the elevated temperature. Bands of components of the mixture exiting the column were analyzed by a thermal conductivity (i.e., hot wire) detector upon elution. The resulting chromatogram is set forth in FIG. 5. Integration of the peaks appearing in FIG. 5 provided the analysis of the mixture set forth in Table 1. As indicated by peak width, the efficiency of the column was approximately three times that of a conventional packed carbon column. As measured by carbon dioxide equilibria, the column contained the equivalent of 12,524 equilibrium stages.

TABLE 1

| # | COMPONENT | AREA % | RT | AREA BC |
|---|---|---|---|---|
| 1 | Nitrogen | 9.829 | 2.81 | 611277 02 |
| 2 | Nitrogen | 32.56 | 2.9 | 2024922 02 |
| 3 | Nitrogen | 51.648 | 2.9 | 3212010 02 |
| 4 | Carbon Monoxide | 1.166 | 3.21 | 72484 03 |
| 5 | Methane | 0.679 | 4.78 | 42205 01 |
| 6 | Carbon Dioxide | 1.099 | 6.66 | 68371 01 |
| 7 | Acetylene | 0.867 | 8.45 | 53917 01 |
| 8 | Ethylene | 1.045 | 9.56 | 64963 01 |
| 9 | Ethane | 1.108 | 10.33 | 68902 01 |

EXAMPLE 3

Figure 6:
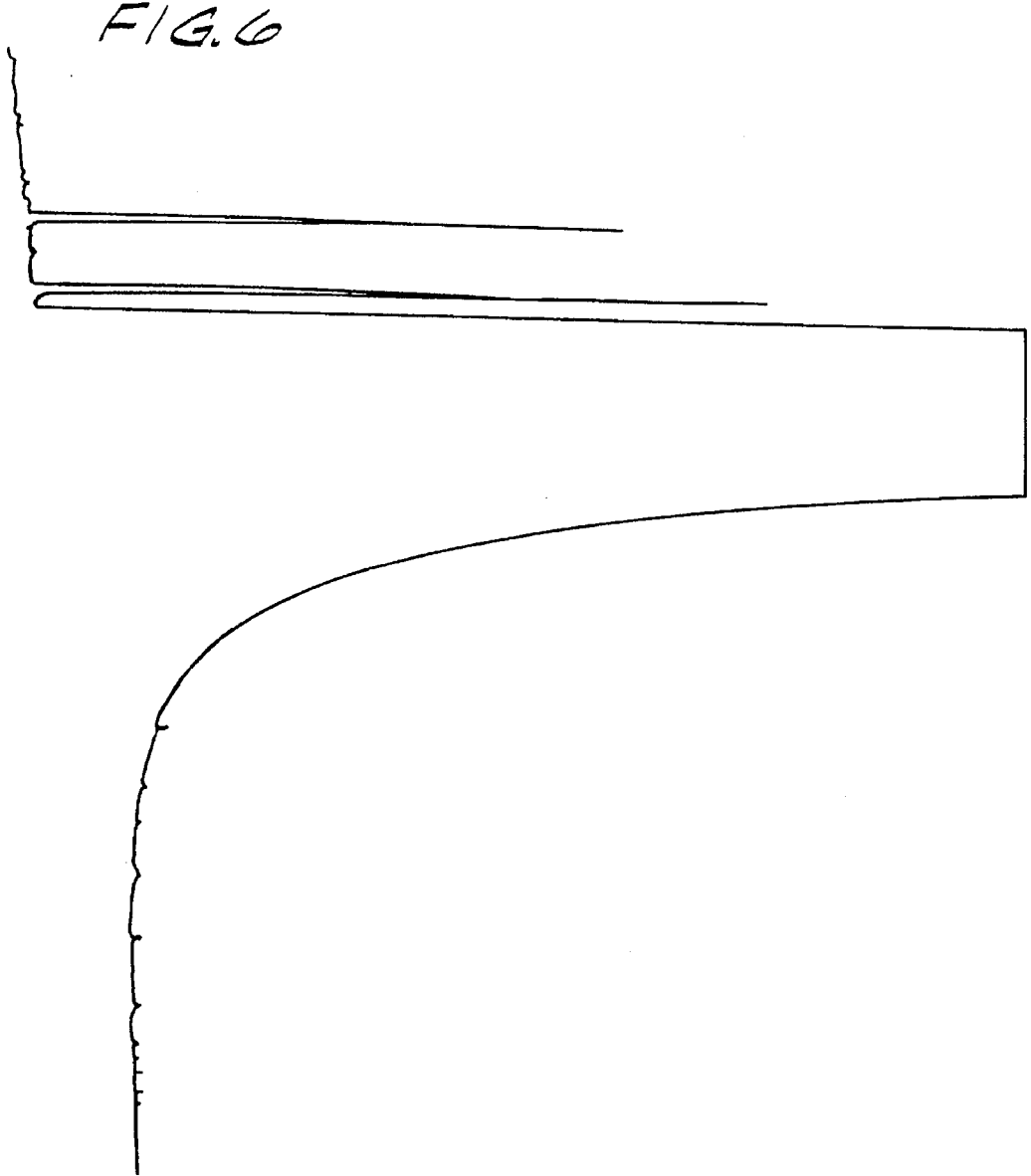

Using a column of the type prepared in Example 1, a specimen of ethylene gas was analyzed for trace quantities of acetylene. The analysis was conducted generally in the manner described in Example 2. Helium eluent was passed through the column at a flow rate of 3.00 mL/min. The column temperature was maintained at 165° C. during elution. Column pressure was 6.0 psig. The resulting chromatogram is set forth in FIG. 6.

EXAMPLE 4

Figure 7:

Using a column of the type prepared in Example 1, a formalin solution was analyzed for water, formaldehyde and methanol content. The analysis was conducted generally in the manner described in Example 2. Helium eluent was passed through the column at a flow rate of 3.00 mL/min. Elution was carried out isothermally at a temperature of 220° C. The pressure in the column was 8.0 psig. The resulting chromatogram is set forth in FIG. 7.

EXAMPLE 5

Figure 8:
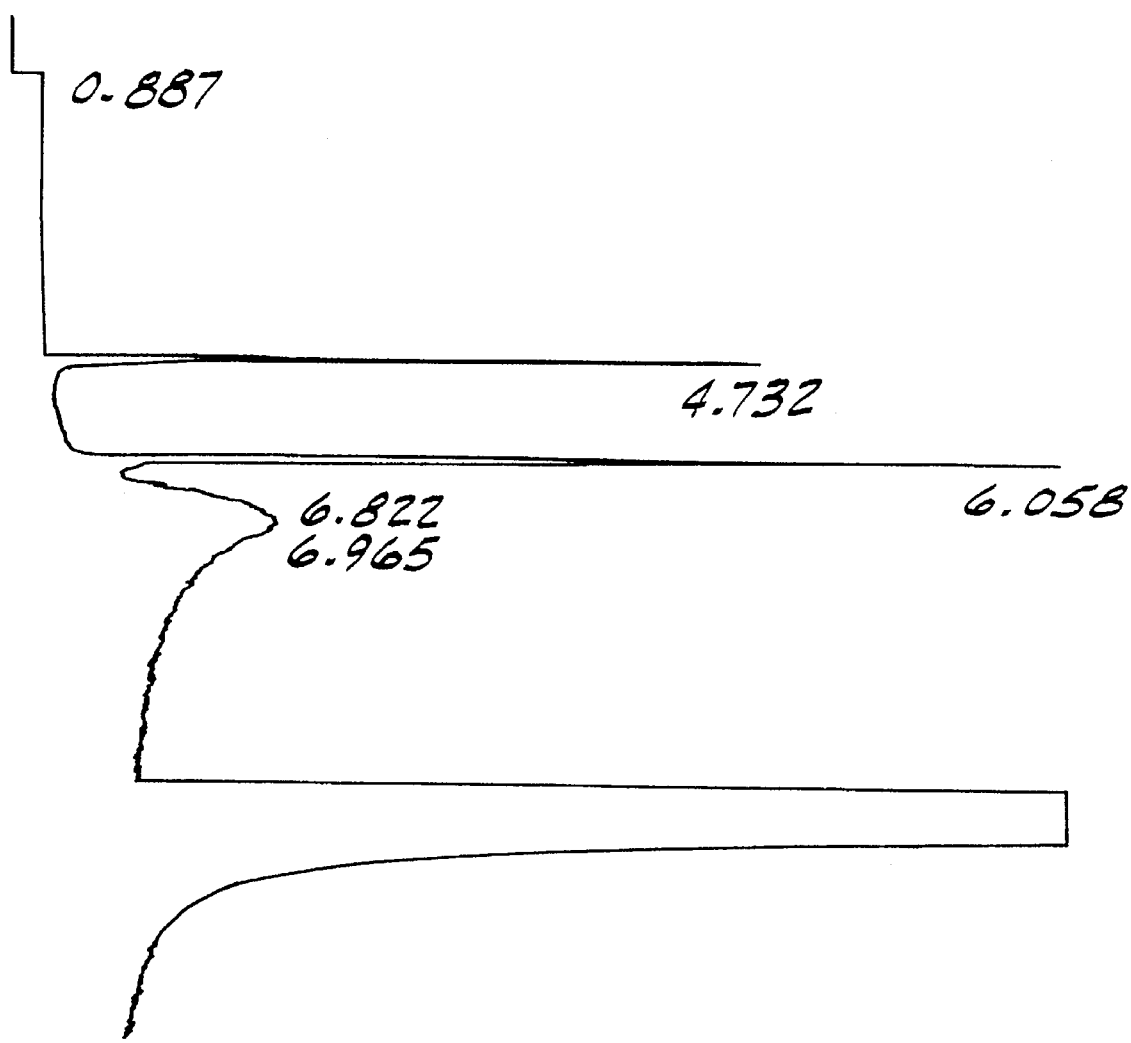

Using the method generally described in Example 2, a light sulfur gas mixture was analyzed using a PLOT column similar to that described in Example 1. Dimensions of the column were 0.53 mm I.D.×15 meters in length. During elution, the temperature was held at 50° C. for one minute, then ramped to 250° C. at a rate of 24° C./min. Helium was passed through the column at a flow rate of 3.0 mL/min, and the pressure was observed to rise from 3.0 psig at 50° C. to 10.0 psig at 250° C. The resulting chromatogram is set forth in FIG. 8.

EXAMPLE 6

Dichloromethane (2.0 mL) was mixed with a polymethylhydro-dimethyl siloxane glue having a molecular weight of 200,000 Daltons, in which 5% of $R^1$ to $R^9$ are hydrogen, the remainder of $R^1$ to $R^9$ are methyl and m/(m+n) is 0.05 (80 mg), and the resulting mixture was sonicated for approximately 2.0 hours to dissolve the siloxane in the solvent. A particulate zeolite molecular sieve (150 mg) was weighed out into a separate vial, and the solution of siloxane in dichloromethane was added to the vial containing the zeolite. The resulting slurry was sonicated for 1.0 hour to uniformly suspend the zeolite in the solution. The sonicated slurry was then transferred to a reservoir for use in providing a porous layer coating on the inside wall of the tubular glass column having an I.D. of 0.53 mm and a length of 30 meters.

A flow of nitrogen was established in the column at a pressure of approximately 30 psig and the slurry of zeolite in siloxane solution flowed by gravity and nitrogen pressure through the column from the reservoir. The suspension was allowed to pass entirely through the column, providing a coating of zeolite in siloxane on the internal glass wall. Effluent siloxane suspension was collected in a dispensing vial. After drainage of the effluent had substantially ceased, the column was placed in an oven and heated at 260° C. for about 10 minutes under a nitrogen purge at a pressure of about 20 psig. Reaction of the siloxane polymer with both the zeolite and the glass resulted in a zeolite coating on the interior surface of the column which was strongly bonded to the glass via a webbing of the siloxane.

This procedure was repeated multiple times to provide a column having multiple layers of zeolite particles bound to and embedded in a porous siloxane polymer webbing that was in turn bonded to the glass.

EXAMPLE 7

Figure 11:
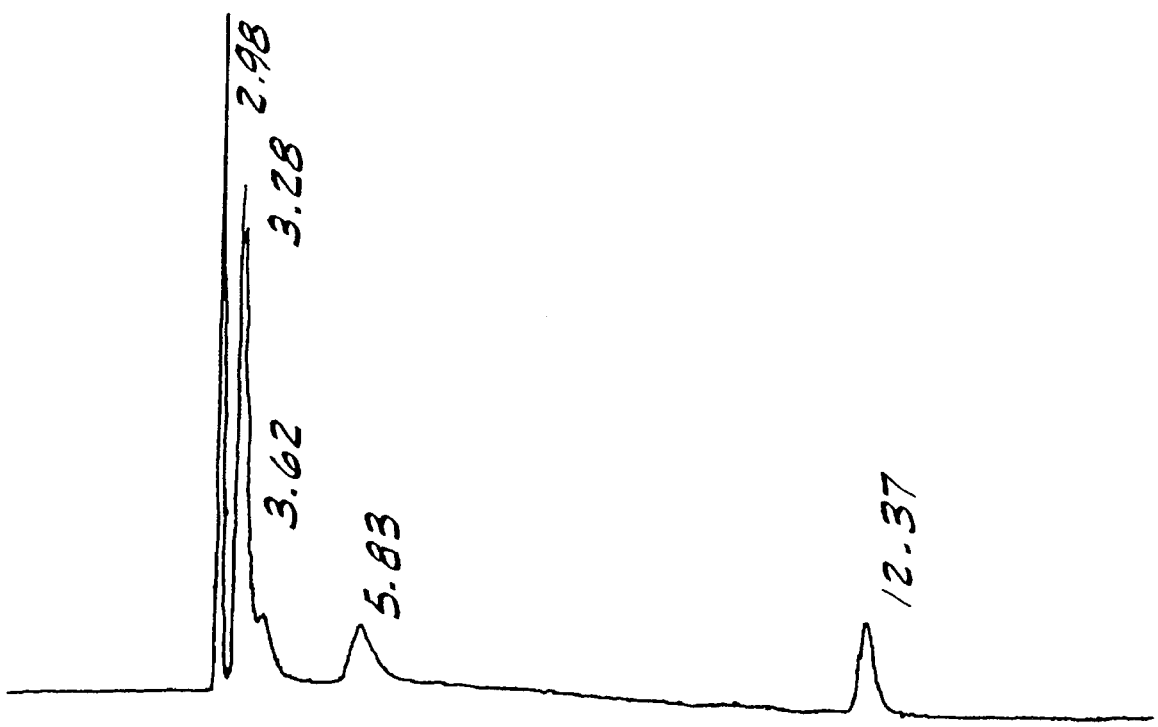
FIGS. 11 to 19 are further chromatograms obtained by gas chromatography of a variety of mixtures using PLOT columns of the type illustrated in FIGS. 1 and 2.

Using the column prepared in the manner described in Example 6, a gas mixture containing oxygen, argon, nitrogen, methane, carbon monoxide, and carbon dioxide was subjected to chromatographic separation. The sample was injected at the column inlet and caused to flow through the column by a mobile phase comprising helium. The helium eluent was passed through the column at a flow rate of 3.0 mL per minute. During elution, the column was maintained at a temperature of 35° C. and a pressure of 2.0 psig. Bands of components of the mixture exiting the column were analyzed by a thermal conductivity (i.e., hot wire) detector upon elution. The resulting chromatogram is set forth in FIG. 11.

EXAMPLE 8

Figure 12:
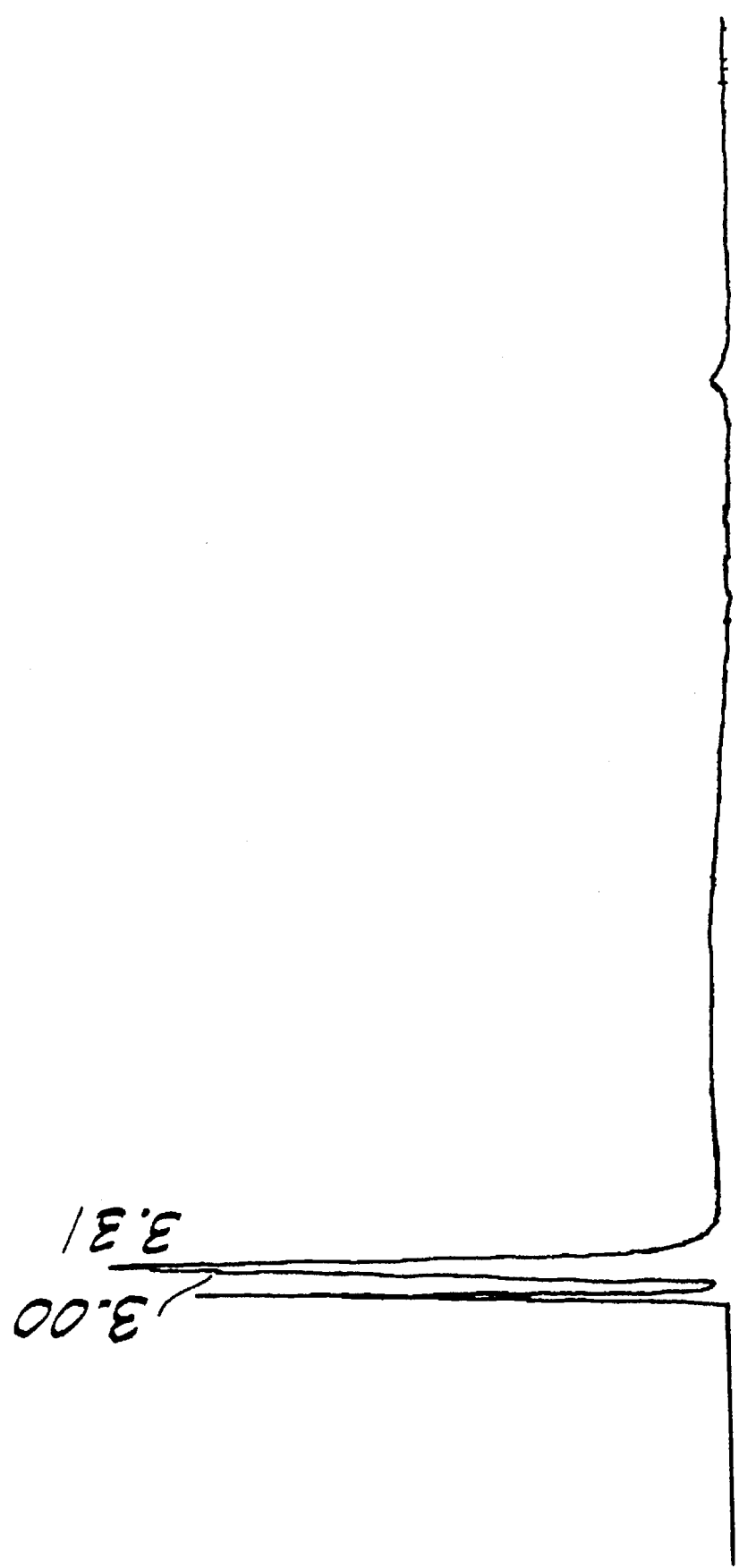

Using a zeolite column of the type prepared in Example 6, room air was subjected to chromatographic analysis. The eluent was helium, passed through the column at a flow of 3.0 mL per minute. Elution was conducted at a temperature of 35° C. and 2.0 psig. Analysis was by thermal conductivity. The resulting chromatograph is set forth in FIG. 12.

EXAMPLE 9

Dichloromethane (2.0 mL) was mixed with a polymethylhydro-dimethyl siloxane glue having a molecular weight of 210,000 Daltons, in which 5% of $R^1$ to $R^9$ are hydrogen, the remainder of $R^1$ to $R^9$ are methyl and m/(m+n) is 0.05 (60 mg), and the resulting mixture was sonicated for approximately 20 hours to dissolve the siloxane in the solvent. Particulate styrene-divinylbenzene polymer of the type sold under the trade designation SUPELPAK# by Supelco, Inc. of Bellefonte, Pa. (60 mg) was weighed out into a separate vial, and the solution of siloxane in dichloromethane added to the vial containing the styrene-divinylbenzene polymer. The resulting slurry was sonicated for 1.0 hour to uniformly suspend the porous polymer in the solution. The sonicated slurry was then transferred to a reservoir for use in providing a porous polymer layer coating on the inside wall of a tubular glass column having an I.D. of 0.53 mm and a length of 30 meters.

A flow of nitrogen was established in the column at a pressure of approximately 30 psig and the slurry of styrene-divinylbenzene copolymer in the siloxane solution flowed by gravity and nitrogen pressure through the column from the reservoir. The suspension was allowed to pass entirely through the column providing a coating of porous styrene-divinylbenzene copolymer in siloxane on the internal glass wall. Effluent siloxane suspension was collected in a dispensing vial. After drainage of the effluent had substantially ceased, the column was placed in an oven, and heated at 260° C. for about 10 minutes under a nitrogen purge at a pressure of about 20 psig. Reaction of the siloxane polymer with both the styrene-divinylbenzene polymer and the glass resulted in a porous polymer coating on the interior surface of the column which was strongly bonded to the glass via a webbing of the siloxane.

This procedure was repeated multiple times to provide a column having multiple layers of porous styrene-divinylbenzene polymer bound to an embedded in a porous siloxane polymer webbing that was in turn bounded to the glass.

EXAMPLE 10

Figure 13:
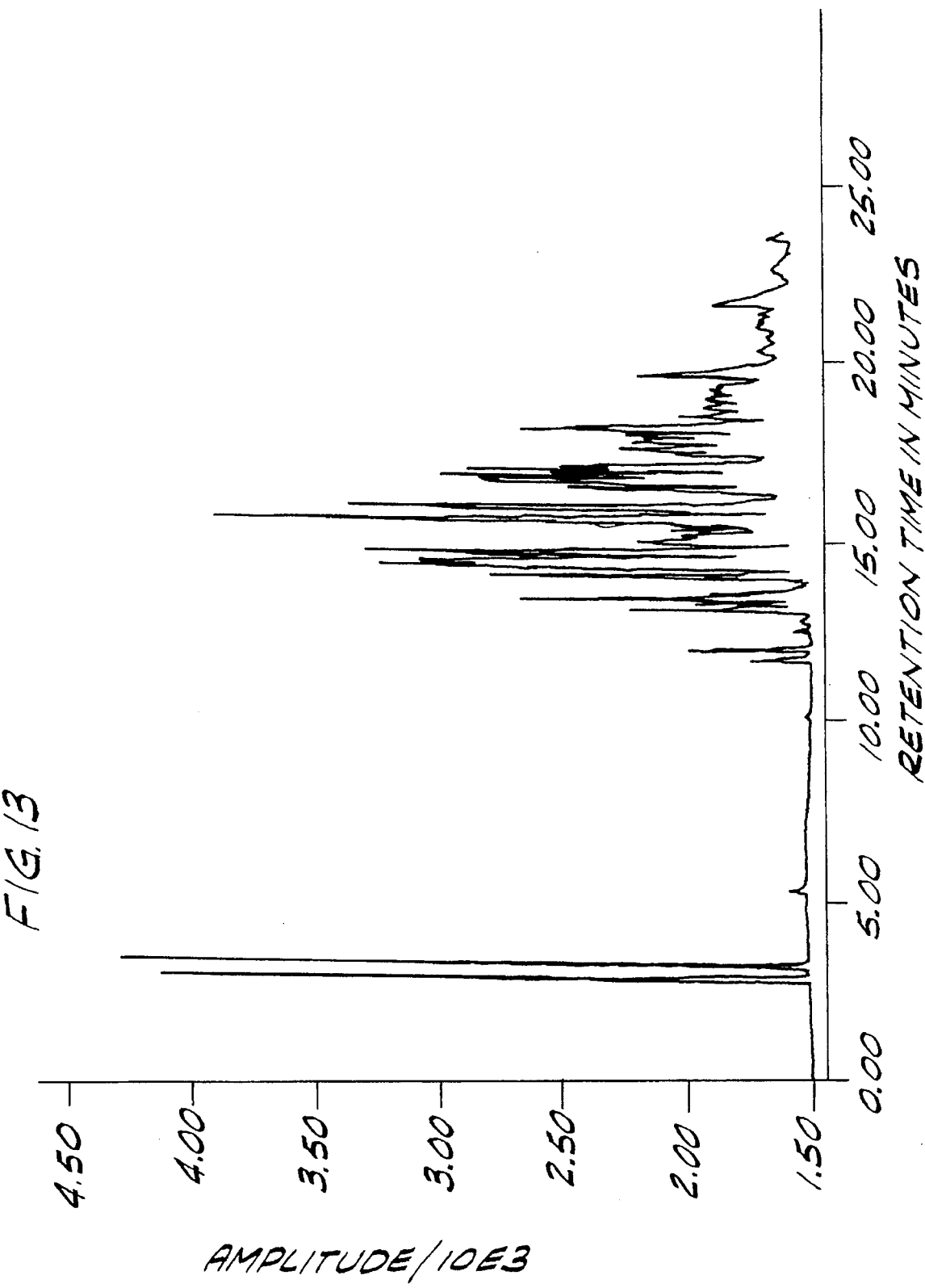

Using the column prepared in the manner described in Example 9, a gas mixture comprising carbon dioxide and gasoline vapor was subjected to chromatographic separation. The sample was injected at the column inlet and caused to flow through the column by mobile phase comprising helium. The helium eluent was passed through the column at a flow rate of 3.0 mL per minute. Elution was conducted at a temperature of 35°–250° C. and a pressure of 3.0 to 15 psig. Bands of components of the mixture exiting the column were analyzed by a thermal conductivity detector upon elution. The resulting chromatogram is set forth in FIG. 13.

EXAMPLE 11

Figure 14:
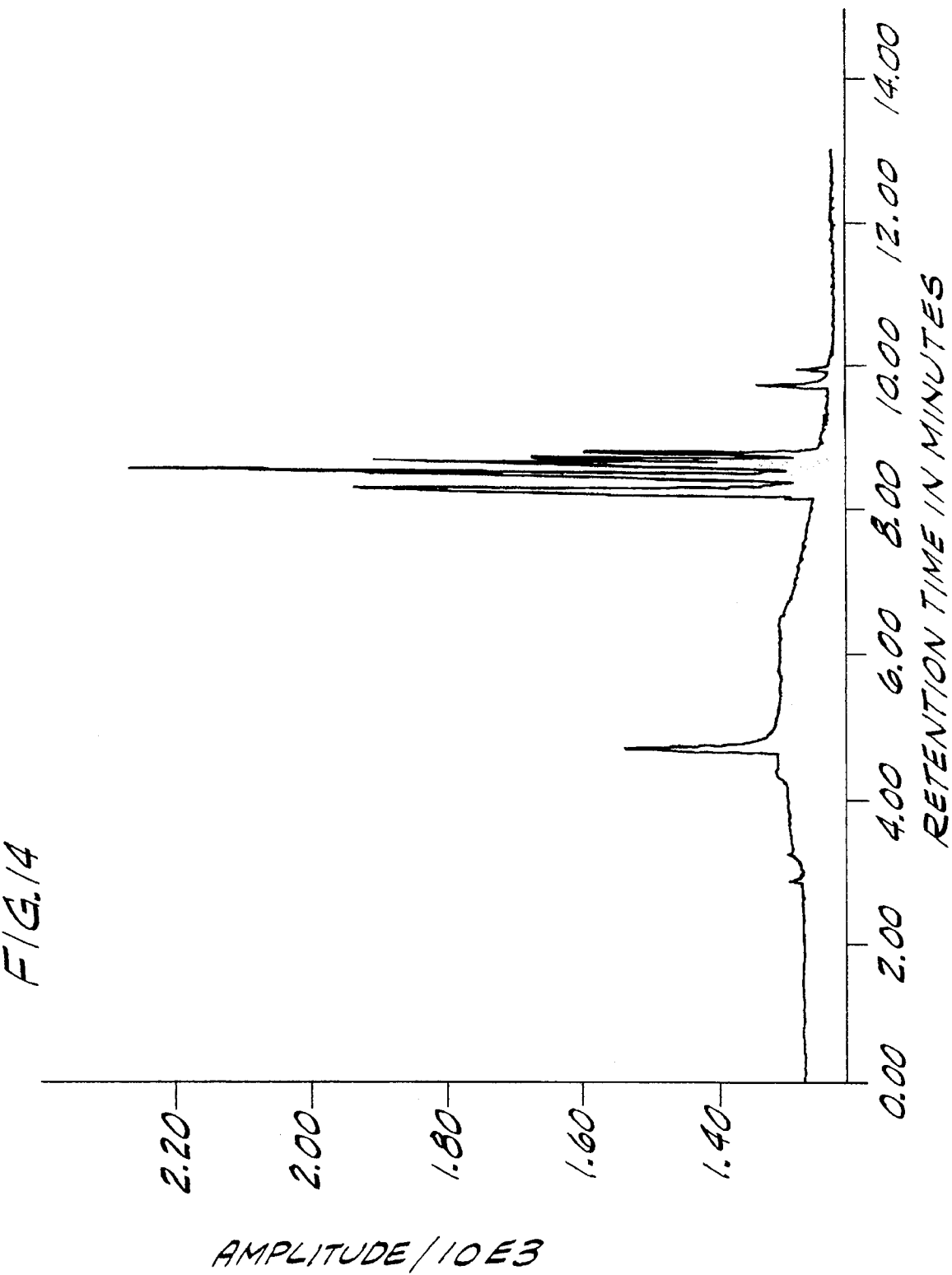

Using a column of the type prepared in Example 9, a gas mixture comprising carbon dioxide and $C_4$ hydrocarbons was subjected to chromatographic separation. The analysis was conducted generally in the manner described in Example 10. helium eluent was passed through the column at a flow rate of 3.0 mL per minute. The elution was conducted at 35° C. to 150° C. and 2.0–10.0 psig. The resulting chromatogram is set forth in FIG. 14.

EXAMPLE 12

Figure 15:
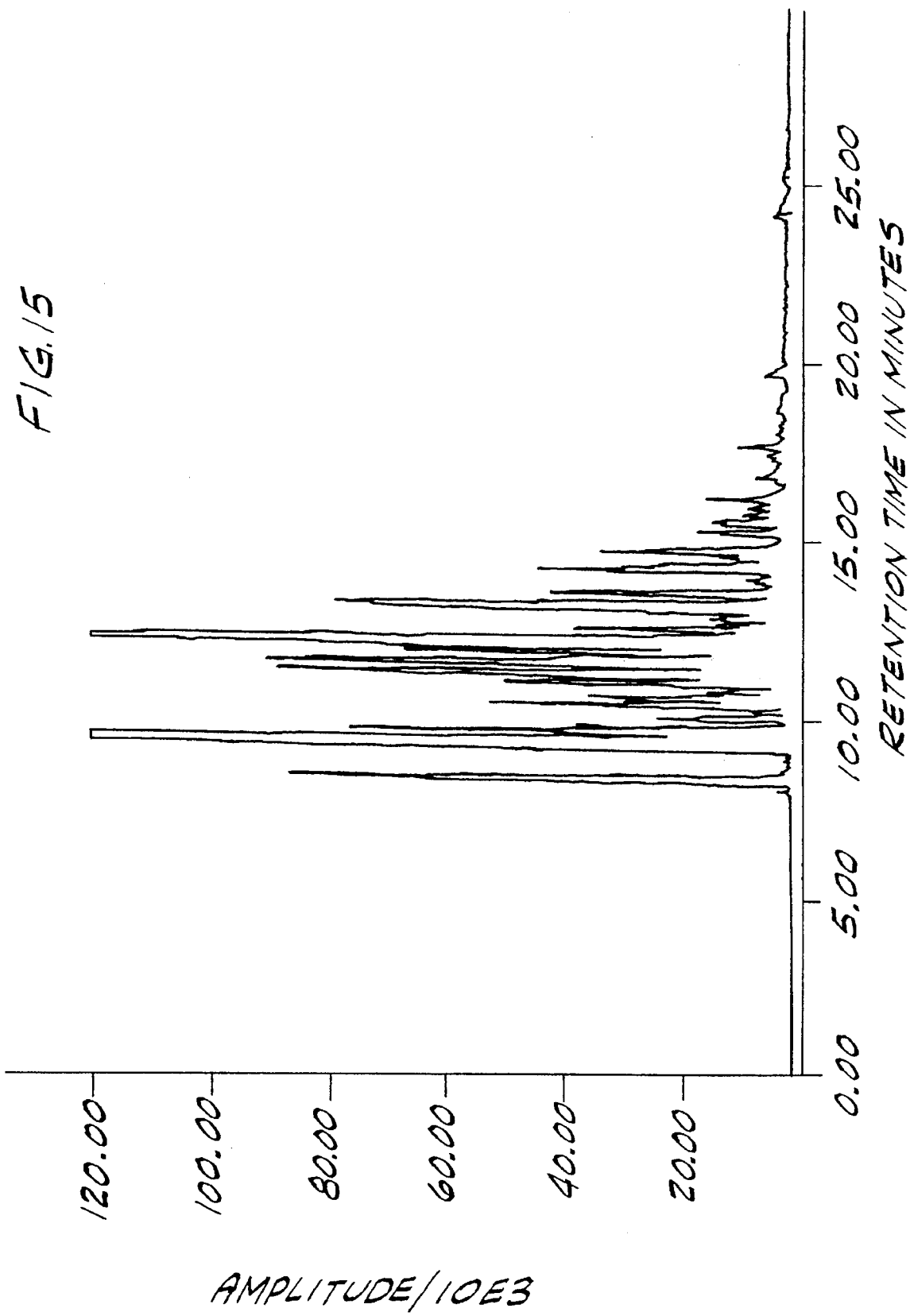

Using the column prepared in the manner described in Example 9, a gas mixture comprising vaporized jet fuel No. 4 was subjected to chromatographic separation. The analysis was conducted generally in the manner described in Example 10. Helium eluent was passed through the column at a flow rate of 3.0 mL/min. The column was operated at a temperature of 35°–2000° C. and a pressure of 3.0–75 psig during the elution. The resulting chromatogram is set forth in FIG. 15.

EXAMPLE 13

Figure 16:
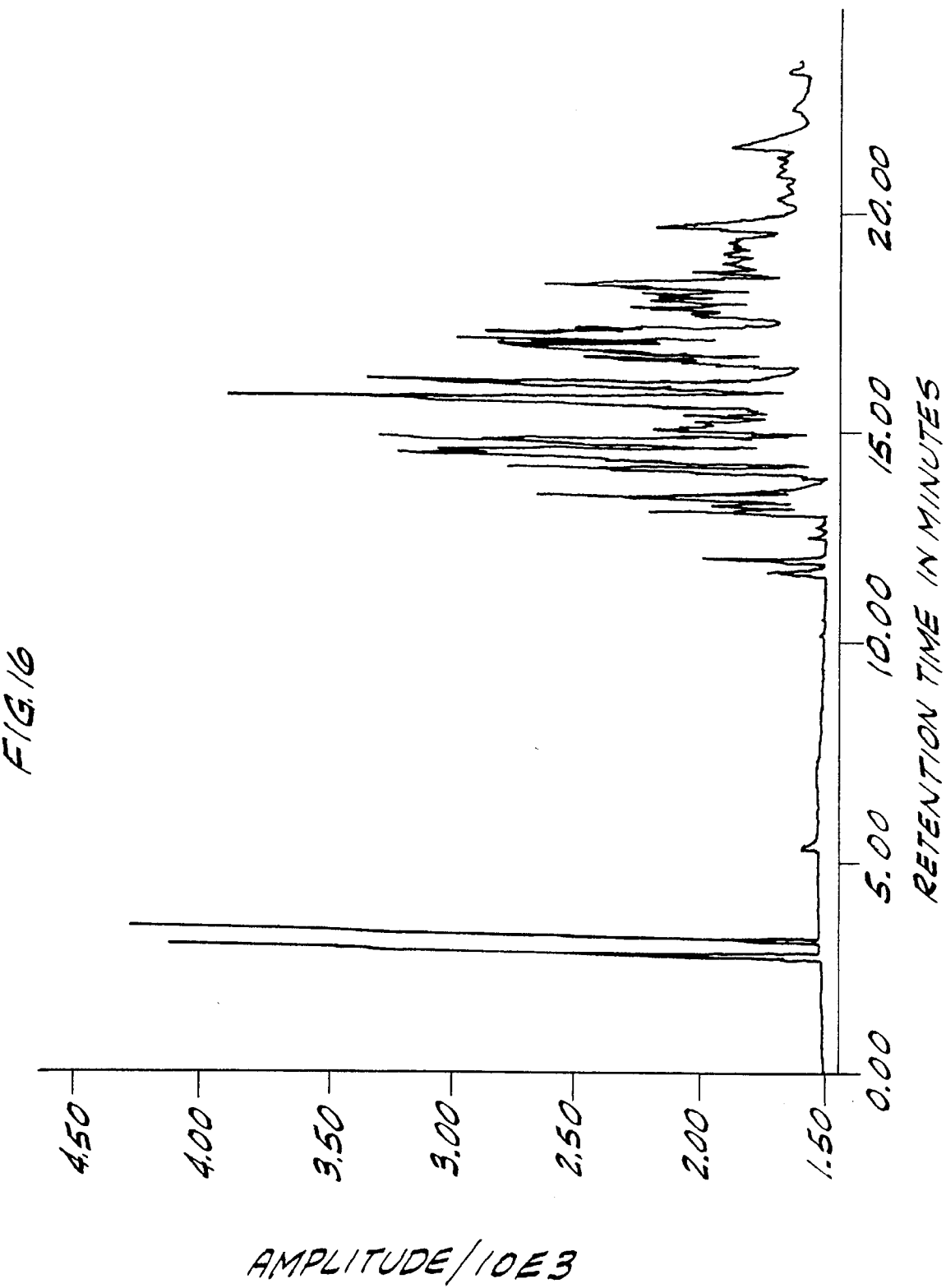

Using the column prepared in the manner described in Example 9, carbon dioxide and vaporized jet fuel No. 4 were subjected to chromatographic separation. The analysis was conducted generally in the manner described in Example 10. Helium eluent was passed through the column at a flow rate of 3.0 mL/min. The column was operated at a temperature of 35° C. to 250° C. and a pressure of 2.0–15 psig during the elution. The resulting chromatogram is set forth in FIG. 16.

EXAMPLE 14

Figure 17:
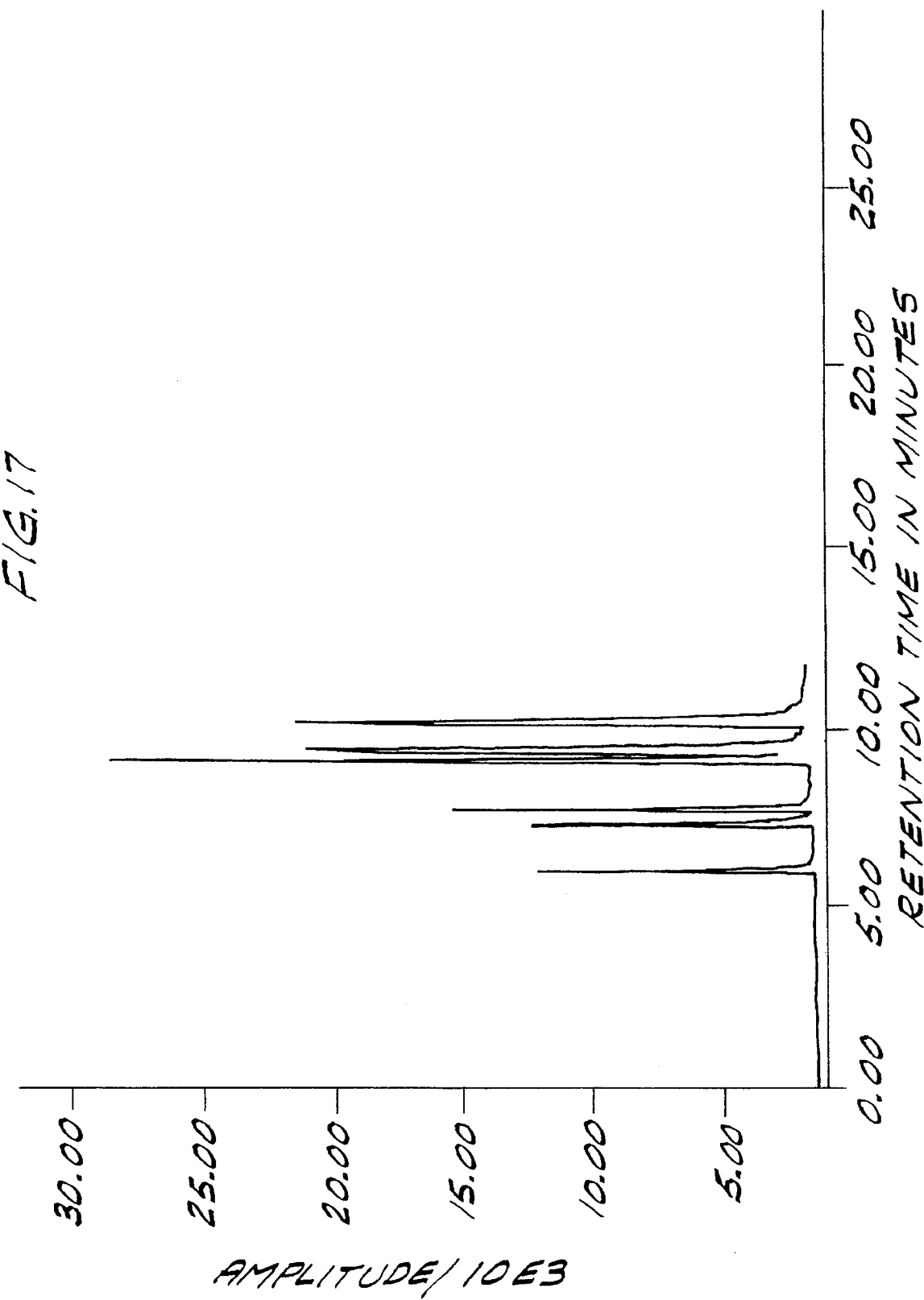

Using the column prepared in the manner described in Example 9, a gas mixture comprising $C_3$ alcohol vapors was subjected to chromatographic separation. The analysis was conducted generally in the manner described in Example 10. Helium eluent was passed through the column at a flow rate of 3.0 mL/min. The column was operated at a temperature of 35° C. to 140° C. and a pressure of 3.0–14 psig during the elution. The resulting chromatogram is set forth in FIG. 17.

EXAMPLE 15

Figure 18:
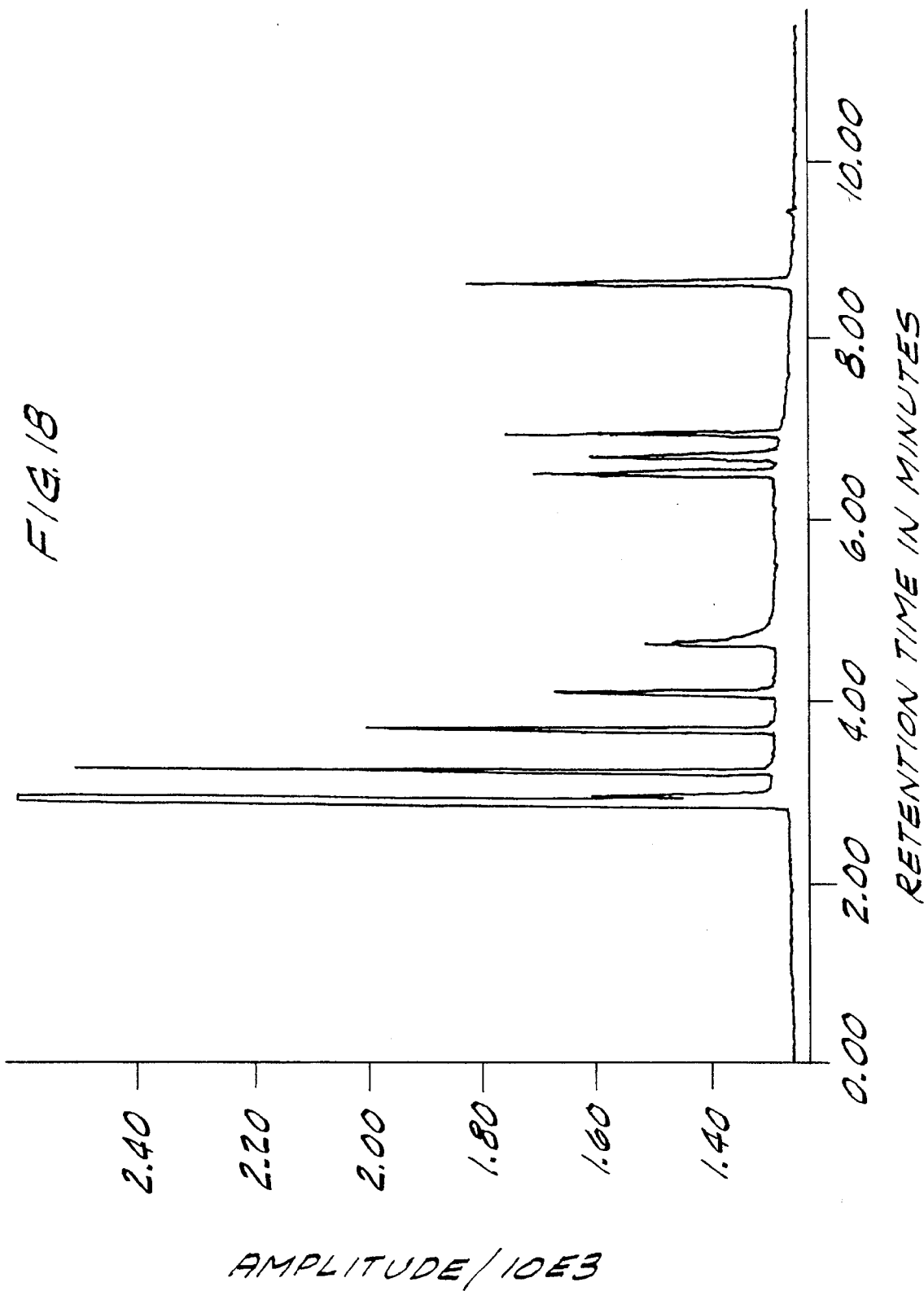

Using the column prepared in the manner described in Example 9, a gas mixture containing permanent gases (air), $C_3$ hydrocarbons and $C_4$ hydrocarbons was subjected to chromatographic separation. The analysis was conducted generally in the manner described in Example 10. Helium eluent was passed through the column at a flow rate of 3.0 mL/min. The column was operated at a temperature of 35° C. and a pressure of 2.0–15 psig during the elution. The resulting chromatogram is set forth in FIG. 18.

EXAMPLE 16

Tetrahydrofuran (2.0 mL) was mixed with a polymethylhydro-dimethyl siloxane glue having a molecular weight of 210,000 Daltons, in which 5% of $R^1$ to $R^9$ are hydrogen, the remainder of $R^1$ to $R^9$ are methyl, and $m/(m+n)$ is 0.05 (80 mg), and the resulting mixture was sonicated for approximately 2.0 hours to dissolve the siloxane in the solvent. Particulate activated alumina (80 mg) was weighed out into a separate vial, and the solution of siloxane and THF added to the vial containing the activated alumina. The resulting slurry was sonicated for 2.0 hours to uniformly suspend the alumina in the solution. The sonicated slurry was then transferred to a reservoir for use in providing a porous layer coating on the inside wall of the tubular glass column having an I.D. of 0.53 μm and a length of 30 meters.

A flow of nitrogen was established in the column at a pressure of approximately 30 psig and the slurry of alumina in siloxane solution flowed by gravity and nitrogen pressure through the column from the reservoir. The suspension was allowed to pass entirely through the column providing a coating of alumina in siloxane on the internal glass wall. The effluent siloxane suspension was collected in the dispensing vial. After drainage of the effluent had substantially ceased, the column was placed in an oven and heated at 260° C. for about 10 minutes under a nitrogen purge at a pressure of about 20 psig. Reaction of the siloxane polymer with both the alumina and the glass resulted in an alumina coating on the interior surface of the column which was strongly bonded to the glass via a webbing of the siloxane.

This procedure was repeated multiple times to provide a column having multiple layers of alumina bound to and embedded in a porous siloxane polymer webbing that was in turn bonded to the glass.

EXAMPLE 17

Figure 19:
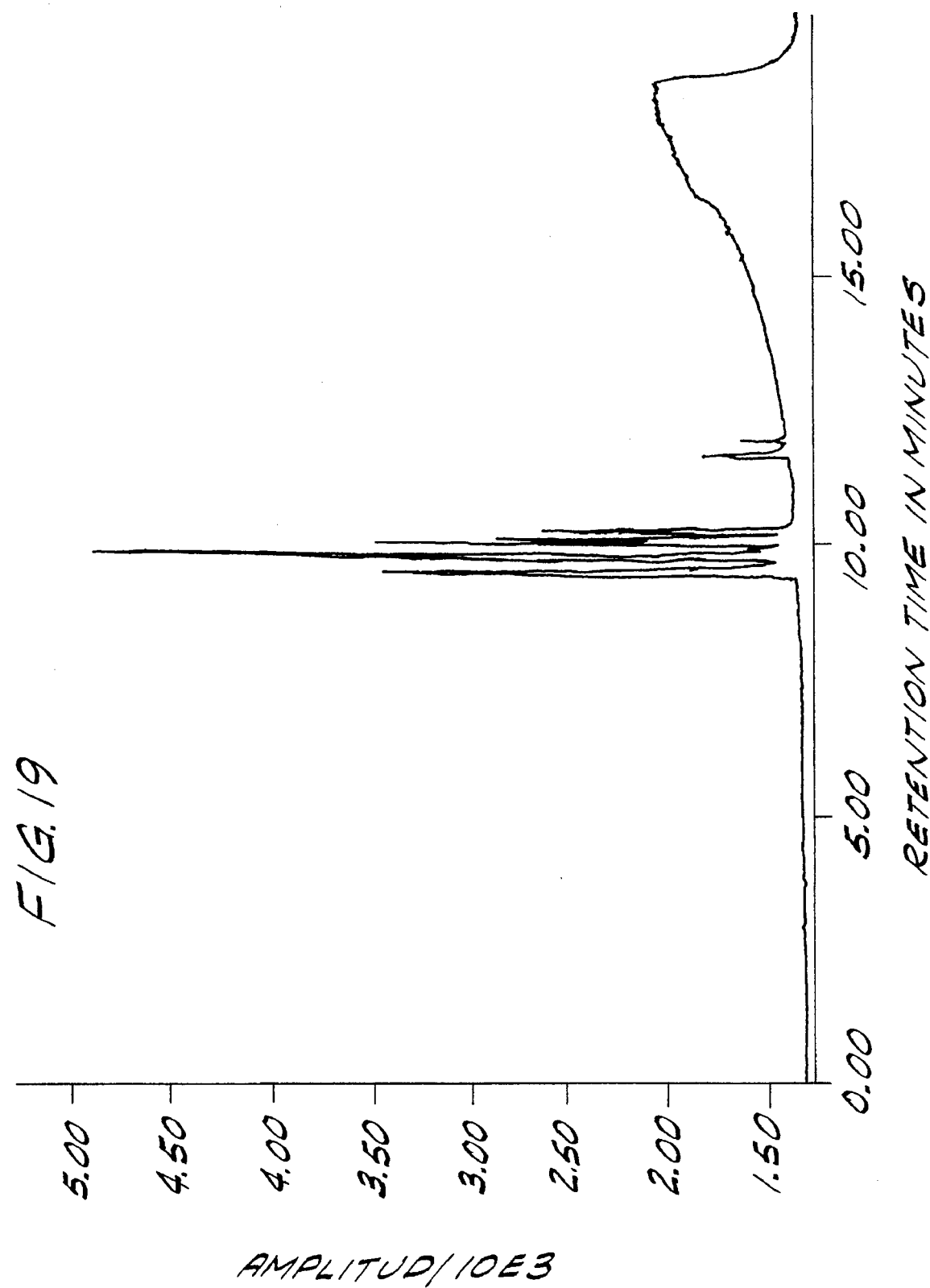

Using the column prepared in the manner described in Example 16, a gas mixture comprising $C_4$ hydrocarbons was subjected to chromatographic separation. The sample was injected at the column inlet and caused to flow through the column by a mobile phase comprising helium. The helium eluent was passed through the column at a flow rate of 3.0 mL per minute. During elution, the column temperature and was at 35°–250° C. and the pressure at 3.0–20 psig. Bands of components of the mixture exiting the column were analyzed by a thermal conductivity detector upon elution. The resulting chromatogram is set forth in FIG. 19.

What is claimed is:

1. A composition comprising a substrate having a siloxane polymer having bodies of carbonaceous material bonded thereto, said carbonaceous bodies comprising elemental carbon or a polymer comprising a hydrocarbon moiety, said bodies being bonded to said siloxane polymer by direct carbon to silicon bonds between carbon atoms of said bodies and silicon atoms of said siloxane polymer.

2. A composition as set forth in claim 1 wherein said bonds are contained in a moiety comprising:

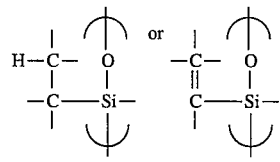

in which the carbon to silicon bond is at the surface of a carbon body.

3. A composition as set forth in claim 1 wherein said carbonaceous bodies are porous.

4. A structure comprising bodies having a functional surface property bonded to a substrate via a siloxane polymer adhesive, said bodies comprising a nucleophilic composition bonded directly to silicon atoms of said siloxane polymer.

5. A structure as set forth in claim 4 wherein bonding of said nucleophilic composition to said siloxane polymer comprises covalent bonding means selected from the group consisting of direct bonds between atoms of said nucleophilic composition and silicon atoms of said siloxane polymer and linkages that consist of an oxygen atom bonded to both an atom of said nucleophilic composition and a silicon atom of said siloxane polymer.

6. A structure as set forth in claim 5 comprising an active surface on which other materials can be adsorbed, said structure comprising adsorbent bodies adhered to said substrate via said siloxane polymer adhesive, said adsorbent bodies comprising a material selected from the group consisting of carbon, alumina, silica, zeolite and a polymer comprising a hydrocarbon moiety.

7. A structure as set forth in claim 6 wherein said adsorbent bodies are porous.

8. A structure as set forth in claim 6 wherein said adsorbent bodies comprise a material selected from the group consisting of carbon and a polymer comprising a hydrocarbon moiety, said bodies being bonded to said siloxane polymer by direct carbon to silicon bonds.

9. A structure as set forth in claim 8 comprising a vitreous substrate containing surface silanol residues to which are bonded a siloxane polymer, carbon bodies being bonded to said siloxane polymer by direct carbon to silicon bonds.

10. A structure as set forth in claim 9 wherein substrate silicon atoms are bonded to said siloxane polymer via Si—O—Si bonds, and said direct carbon to silicon bonds are contained in a moiety comprising:

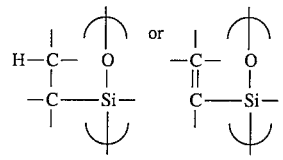

in which the carbon to carbon double bond is at the surface of a carbon body.

11. A structure as set forth in claim 10 wherein said moiety comprises:

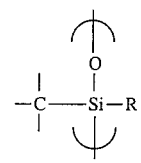

wherein R is hydrogen, substituted or unsubstituted hydrocarbyl, nitro or cyano.

12. A structure as set forth in claim 10 wherein the molecular weight of said siloxane polymer is between about 80,000 and about 2,000,000.

13. A structure as set forth in claim 9 wherein said vitreous substrate comprises glass.

14. A structure as set forth in claim 13 wherein said vitreous substrate comprises the inside wall of a glass column.

15. A structure as set forth in claim 14 wherein said vitreous substrate comprises the surface of a glass fiber.

16. A structure as set forth in claim 4 comprising a siloxane polymer network extending along the surface of said substrate, said bodies being distributed through said network.

17. A structure as set forth in claim 16 wherein said network further extends outwardly from said substrate surface in a plurality of layers, carbon particles being distributed within said network both laterally and vertically with respect to said substrate surface.

18. A structure as set forth in claim 4 wherein said carbon particles have a B.E.T. surface area of between about 1.0 and about 1500 m² per gram.

19. A structure as set forth in claim 4 wherein said substrate has a surface comprising a nucleophilic composition.

20. A structure as set forth in claim 19 wherein the surface of said substrate comprises a material selected from the group consisting of a metal, a vitreous material and a polymer comprising a hydrocarbon moiety.

* * * * *